US012567482B2

(12) United States Patent
Mitjans et al.

(10) Patent No.: US 12,567,482 B2
(45) Date of Patent: Mar. 3, 2026

(54) SURVEY AND SUGGESTION SYSTEM

(71) Applicant: Evernorth Strategic Development, Inc., St. Louis, MO (US)

(72) Inventors: Milton D. Mitjans, Wesley Chapel, FL (US); Kevin Herzig, Fort Myers, FL (US)

(73) Assignee: Evernorth Strategic Development, Inc., St. Louis, MO (US)

( * ) Notice: Subject to any disclaimer, the term of this patent is extended or adjusted under 35 U.S.C. 154(b) by 328 days.

(21) Appl. No.: 18/204,798

(22) Filed: Jun. 1, 2023

(65) Prior Publication Data

US 2023/0395204 A1     Dec. 7, 2023

Related U.S. Application Data

(60) Provisional application No. 63/348,329, filed on Jun. 2, 2022.

(51) Int. Cl.
*G16H 10/20* (2018.01)
*G06N 3/0455* (2023.01)

(52) U.S. Cl.
CPC ........... *G16H 10/20* (2018.01); *G06N 3/0455* (2023.01)

(58) Field of Classification Search
CPC ........ G16H 10/20; G16H 20/00; G16H 40/67; G16H 50/20; G16H 50/70; G06N 3/0455;
(Continued)

(56) References Cited

U.S. PATENT DOCUMENTS 6,999,987 B1     2/2006  Billingsley
7,100,197 B2     8/2006  Rail
(Continued)

FOREIGN PATENT DOCUMENTS

CN     109671475  A     4/2019
CN     110046186  A     7/2019
(Continued)

OTHER PUBLICATIONS

M. J. Kargar and A. Oveissi, "An open model for question answering systems based on Crowdsourcing," 2017 3th International Conference on Web Research (ICWR), Tehran, Iran, 2017, pp. 122-127, doi: 10.1109/ICWR.2017.7959316. (Year: 2017).*
Z. Liu and B. J. Jansen, "Question and Answering Made Interactive: An Exploration of Interactions in Social Q&A," 2013 International Conference on Social Intelligence and Technology, State College, PA, USA, 2013, pp. 1-10, doi: 10.1109/SOCIETY.2013.16. (Year: 2013).*
Generating Multiple Diverse Responses for Short-Text Conversation, by Jun Gao, Wei Bi, Xiaojiang Liu, Junhui Li., Shuming Shi, arXiv:1811.05696v3 [cs.CL] Feb. 21, 2019. (Year: 2019).*
(Continued)

*Primary Examiner* — Sun M Li
(74) *Attorney, Agent, or Firm* — Jordan IP Law PC

(57) ABSTRACT

Apparatuses, systems, and methods relate to technology to receive a user request from a user device, identify that a plurality of questions is available for presentation on the user device based on the user request and select a first question from the plurality of questions. The technology transmits the first question to the user device, receives a first user reply from the user device, where the first user reply is an answer to the first question and selects a second question from the plurality of questions based on the first user reply. The technology transmits the second question to the user device, receives a second user reply from the user device, where the second user reply is an answer to the second question, determines a user suggestion based on the first and second user replies, and transmits the user suggestion to the user device.

20 Claims, 19 Drawing Sheets

(58) Field of Classification Search
   CPC .......... G06N 3/047; G06N 3/088; G06N 3/09;
                 G06N 5/022; G06N 20/00
   See application file for complete search history.

(56)                    References Cited

U.S. PATENT DOCUMENTS

| | | |
|---|---|---|
| 7,103,556 B2 | 9/2006 | Del Rey |
| 7,433,828 B2 | 10/2008 | Brinkman |
| 7,448,047 B2 | 11/2008 | Poole |
| 7,519,577 B2 | 4/2009 | Brundage |
| 7,707,627 B2 | 4/2010 | Hirsh |
| 7,752,289 B2 | 7/2010 | Kikkawa |
| 7,874,011 B2 | 1/2011 | Boss |
| 7,979,894 B2 | 7/2011 | Royyuru |
| 8,045,475 B2 | 10/2011 | Mohan |
| 8,401,871 B2 | 3/2013 | Fotsch |
| 8,505,077 B2 | 8/2013 | Kulkarni |
| 8,566,121 B2 | 10/2013 | Ramasubramanian |
| 8,826,021 B2 | 9/2014 | Savage |
| 8,924,236 B2 | 12/2014 | Marchosky |
| 8,935,272 B2 | 1/2015 | Ganti |
| 8,955,058 B2 | 2/2015 | Castro |
| 8,979,627 B2 | 3/2015 | Walker |
| 9,195,822 B2 | 11/2015 | Carlson |
| 9,239,834 B2 | 1/2016 | Donabedian |
| 9,244,952 B2 | 1/2016 | Ganti |
| 9,282,425 B2 | 3/2016 | Tomkins |
| 9,305,059 B1 | 4/2016 | Glickman |
| 9,497,178 B2 | 11/2016 | Chow |
| 9,516,008 B2 | 12/2016 | Chow |
| 9,563,784 B2 | 2/2017 | Meredith |
| 9,686,674 B2 | 6/2017 | Lin |
| 9,787,692 B2 | 10/2017 | Peleg |
| 9,836,778 B2 | 12/2017 | Lyman |
| 9,842,034 B2 | 12/2017 | Heliker |
| 9,854,431 B2 | 12/2017 | Lin |
| 9,927,983 B2 | 3/2018 | Benisty |
| 9,977,867 B2 | 5/2018 | Greene |
| 10,027,654 B2 | 7/2018 | Bringer |
| 10,261,695 B2 | 4/2019 | Benisty |
| 10,270,839 B2 | 4/2019 | Andreou |
| 10,311,450 B2 | 6/2019 | Bjelajac |
| 10,380,537 B2 | 8/2019 | Agasti |
| 10,423,356 B2 | 9/2019 | Iyengar |
| 10,437,841 B2 | 10/2019 | Robichaud |
| 10,445,508 B2 | 10/2019 | Sher-Jan |
| 10,475,140 B2 | 11/2019 | Patel |
| 10,484,547 B2 | 11/2019 | Weeks |
| 10,503,746 B2 | 12/2019 | Choudhary |
| 10,515,188 B2 | 12/2019 | Soto |
| 10,565,509 B2 | 2/2020 | London |
| 10,613,964 B2 | 4/2020 | Davis |
| 10,621,880 B2 | 4/2020 | Boguraev |
| 10,629,310 B2 | 4/2020 | Livesay |
| 10,650,430 B2 | 5/2020 | Fine |
| 10,659,399 B2 | 5/2020 | Foerster |
| 10,691,774 B2 | 6/2020 | Thorpe |
| 10,692,159 B2 | 6/2020 | Charkov |
| 10,706,971 B2 | 7/2020 | Ramaci |
| 10,720,232 B2 | 7/2020 | Giordano |
| 10,726,079 B2 | 7/2020 | Makaremi |
| 10,733,546 B2 | 8/2020 | Pilkington |
| 10,733,903 B2 | 8/2020 | Kurowski |
| 10,811,006 B2 | 10/2020 | Yamagami |
| 10,817,589 B2 | 10/2020 | Lara |
| 10,834,221 B2 | 11/2020 | Tong |
| 10,860,655 B2 | 12/2020 | Murphey |
| 10,915,605 B2 | 2/2021 | Stadler |
| 10,964,430 B2 | 3/2021 | Willard |
| 10,978,185 B2 | 4/2021 | Aagesen |
| 10,997,251 B2 | 5/2021 | Tran |
| 11,107,563 B2 | 8/2021 | Vogt |
| 11,923,079 B1 | 3/2024 | Schilling |
| 2002/0065682 A1 | 5/2002 | Goldenberg |
| 2002/0194024 A1 | 12/2002 | Kleinschmidt |

| | | | |
|---|---|---|---|
| 2004/0267704 A1 | 12/2004 | Subramanian | |
| 2005/0159986 A1 | 7/2005 | Breeland | |
| 2006/0154642 A1 | 7/2006 | Scannell, Jr. | |
| 2006/0241972 A1 | 10/2006 | Lang | |
| 2006/0271405 A1 | 11/2006 | Cipolle | |
| 2007/0038474 A1 | 2/2007 | Halsted | |
| 2007/0219795 A1 | 9/2007 | Park | |
| 2007/0219958 A1 | 9/2007 | Park | |
| 2007/0239516 A1 | 10/2007 | Smith | |
| 2010/0042578 A1 | 2/2010 | Leuthardt | |
| 2010/0088245 A1 | 4/2010 | Harrison | |
| 2010/0250279 A1 | 9/2010 | Guggenheim | |
| 2011/0246251 A1 | 10/2011 | Saunders | |
| 2013/0103434 A1 | 4/2013 | Cazeaux | |
| 2013/0179178 A1 | 7/2013 | Vemireddy | |
| 2014/0074506 A1 | 3/2014 | Oliver | |
| 2014/0210618 A1 | 7/2014 | Poe | |
| 2014/0214659 A1 | 7/2014 | Hansen | |
| 2014/0249889 A1 | 9/2014 | Park | |
| 2014/0297308 A1 | 10/2014 | Baruch | |
| 2014/0310306 A1 | 10/2014 | Sawczuk | |
| 2014/0316815 A1 | 10/2014 | Chen | |
| 2014/0372137 A1 | 12/2014 | Tryon | |
| 2015/0142459 A1 | 5/2015 | Nichols | |
| 2015/0297078 A1 | 10/2015 | Gross | |
| 2015/0310559 A1 | 10/2015 | Kaafarani | |
| 2015/0339393 A1 | 11/2015 | Chung | |
| 2015/0347681 A1 | 12/2015 | Bartlett, II | |
| 2015/0350611 A1 | 12/2015 | Pearson | |
| 2016/0019316 A1 | 1/2016 | Murphey | |
| 2016/0110523 A1 | 4/2016 | Francois | |
| 2016/0173822 A1 | 6/2016 | Lemmey | |
| 2016/0189317 A1 | 6/2016 | Papandrea | |
| 2017/0011179 A1 | 1/2017 | Arshad | |
| 2017/0032394 A1 | 2/2017 | Stevens | |
| 2017/0180518 A1 | 6/2017 | Choi | |
| 2017/0270532 A1 | 9/2017 | Livesay | |
| 2017/0374568 A1 | 12/2017 | Heath | |
| 2018/0054710 A1 | 2/2018 | Gum | |
| 2018/0101659 A1 | 4/2018 | Ninan | |
| 2018/0268417 A1 | 9/2018 | Livesay | |
| 2018/0293234 A1 | 10/2018 | Resnofendri | |
| 2019/0027248 A1* | 1/2019 | Kataria | H04N 7/183 |
| 2019/0034589 A1 | 1/2019 | Chen | |
| 2019/0034590 A1 | 1/2019 | Oren | |
| 2019/0052720 A1 | 2/2019 | Guo | |
| 2019/0065499 A1 | 2/2019 | Wagstaff | |
| 2019/0074080 A1 | 3/2019 | Appelbaum | |
| 2019/0103173 A1 | 4/2019 | Power | |
| 2019/0138734 A1 | 5/2019 | Sher-Jan | |
| 2019/0156295 A1 | 5/2019 | Lu | |
| 2019/0198181 A1 | 6/2019 | Livesay | |
| 2019/0272925 A1 | 9/2019 | Barrett | |
| 2019/0333638 A1* | 10/2019 | Elidan | G16H 20/40 |
| 2020/0042577 A1 | 2/2020 | Kasa | |
| 2020/0241895 A1 | 7/2020 | Voss | |
| 2020/0251194 A1 | 8/2020 | Vogt | |
| 2020/0258609 A1* | 8/2020 | McMaster | G16H 10/40 |
| 2020/0322703 A1 | 10/2020 | Bures | |
| 2020/0342455 A1 | 10/2020 | Poteet, III | |
| 2021/0057056 A1* | 2/2021 | Chin | G16H 10/40 |
| 2021/0110895 A1* | 4/2021 | Shriberg | G16H 10/20 |
| 2022/0028513 A1 | 1/2022 | Gangaikondan-Iyer | |
| 2022/0261817 A1* | 8/2022 | Ferrucci | G16H 70/20 |
| 2023/0154575 A1* | 5/2023 | Goel | G16H 10/20 |
| | | | 705/3 |
| 2023/0170065 A1* | 6/2023 | De Vries | G16H 50/30 |
| | | | 705/2 |
| 2023/0215282 A1* | 7/2023 | Sastry | G06N 20/00 |
| | | | 434/367 |
| 2023/0393894 A1 | 12/2023 | Herzig | |
| 2023/0395204 A1 | 12/2023 | Mitjans | |
| 2023/0395213 A1 | 12/2023 | Jain | |
| 2023/0395214 A1 | 12/2023 | Needs | |

(56) References Cited

U.S. PATENT DOCUMENTS

| | | | |
|---|---|---|---|
| 2023/0395215 | A1 | 12/2023 | Long |
| 2023/0395243 | A1 | 12/2023 | Teeple |

FOREIGN PATENT DOCUMENTS

| | | | | |
|---|---|---|---|---|
| CN | 110691548 | A | 1/2020 | |
| CN | 113380351 | A | 9/2021 | |
| EP | 3362890 | A1 | 8/2018 | |
| EP | 3489958 | A1 | 5/2019 | |
| EP | 3634204 | A1 | 4/2020 | |
| EP | 3799056 | A1 | 3/2021 | |
| KR | 101575146 | B1 | 12/2015 | |
| KR | 20200003407 | A | 1/2020 | |
| WO | 2001013274 | A2 | 2/2001 | |
| WO | 200120488 | A1 | 3/2001 | |
| WO | 2019022779 | A1 | 1/2019 | |
| WO | WO-2021247792 | A1 * | 12/2021 | ............ G16H 10/20 |

OTHER PUBLICATIONS

Computational Creativity via Assisted Variational Synthesis of Mechanisms Using Deep Generative Models, by Shrinath Deshpande, Anurag Purwar, Journal of Mechanical Design, Dec. 2019, vol. 141 / 121402-1. (Year: 2019).*

M. Nuruzzaman and O. K. Hussain, "A Survey on Chatbot Implementation in Customer Service Industry through Deep Neural Networks," 2018 IEEE 15th International Conference on e-Business Engineering (ICEBE), Xi'an, China, 2018, pp. 54-61, doi: 10.1109/ICEBE.2018.00019. (Year: 2018).*

R. Mu, "A Survey of Recommender Systems Based on Deep Learning," in IEEE Access, vol. 6, pp. 69009-69022, 2018, doi: 10.1109/ACCESS.2018.2880197. (Year: 2018).*

Qualtrics, Question Randomization. https://www.qualtrics.com/support/survey-platform/survey-module/block-option/question-randomization/, accessed Aug. 11, 2020.

* cited by examiner

480

Begin

Begin flow processing based on questionnaire rules

482

Process Responses

484

Is questionnaire completed?    486

488    Select and provide next question

No

Yes

End Engine    490

Generate vector space score    492

Generate a recommendation based on the score

494

Generate error based on flow processing, responses and recommendation

496

Update a neural network based on error

498

End

580

SURVEY AND SUGGESTION SYSTEM

CROSS-REFERENCE TO RELATED APPLICATIONS

The present application claims the benefit of priority to U.S. Patent Application No. 63/348,329 (filed on Jun. 2, 2022), which is hereby incorporated by reference in its entirety.

TECHNICAL FIELD

Embodiments generally relate to a questionnaire and suggestion architecture. In detail, the questionnaire and suggestion platform tracks patient replies to questions of the questionnaire, dynamically adjusts future questions on the fly and in real-time based on the patient replies, and dynamically adjusts patient suggestions in real-time based on the results of the questionnaire.

BACKGROUND

Health can be monitored in a variety of ways. For example, a patient can have certain measurements obtained through medical devices. Such medical devices can include blood pressure cuffs, smart watches, smart scales, etc. In some cases, a patient can be asked a series of questions and provide replies to the questions to gauge a health of the patient.

BRIEF DESCRIPTION OF THE DRAWINGS

The various advantages of the embodiments of the present disclosure will become apparent to one skilled in the art by reading the following specification and appended claims, and by referencing the following drawings, in which:

DETAILED DESCRIPTION

Figure 1:
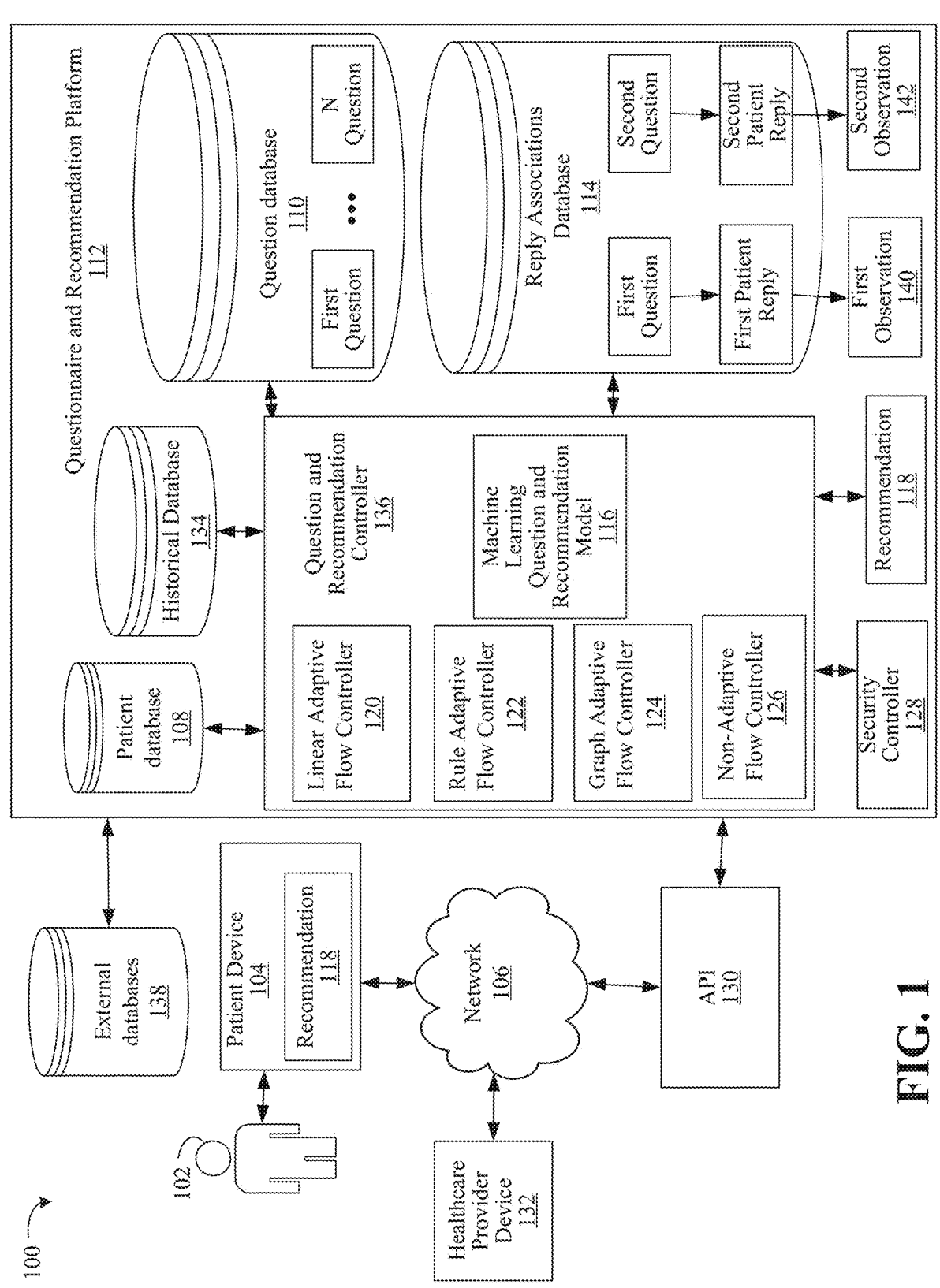
FIG. 1 is a diagram of an example of a questionnaire generation, analysis and treatment process according to an embodiment.

Patient health information can be difficult to track, monitor and analyze. For example, patients can measure certain health parameters (e.g., blood pressure) at a location remote from a health provider's location. The measurements are not necessarily always analyzed by a health provider due to time constraints of the health provider, failure by the patient to provide such measurements to the health provider, etc. Furthermore, health measurements as measured by some health devices (e.g., weight scale, blood pressure cuff, heart rate monitor, smart watch, etc.) will measure specific physical characteristics of the patient, but neglect to measure mental and other physical health aspects of the patient (e.g., mood, feelings, physical pain, discomfort, etc.). For example, a patient can have optimal health readings (e.g., blood pressure, cholesterol, enzymes, etc.) as measured by certain devices, and yet still have health ailments (e.g., experience physical pain and/or have negative mental health).

Some health providers can require a patient to complete a questionnaire (e.g., a survey) to better gauge health ailments. Such questionnaires however are not customized to the patient resulting in extended patient time to complete the questionnaire, extended health provider time to analyze the questionnaires, and potential noncompliance if the patient decides that the questionnaire is irrelevant and/or too lengthy to complete. Moreover, such questionnaires can be outdated and lack certain questions due to the static nature of the questionnaires, resulting in a lack of useable and useful data. For example, as questions of a questionnaire are answered, it can become apparent that the answers are associated with certain conditions. The questionnaire may not be directed to detection and/or analysis of the certain conditions and therefore lacks questions relating to the certain conditions. Thus, the questionnaire can provide little meaningful guidance to a health provider and lack relevancy. Furthermore, health providers employ a subjective analysis that can result in errors, misdiagnoses and/or failure to provide effective recommendations based on the questionnaires.

Moreover, a health provider can misdiagnose or administer a suboptimal treatment plan based on the lack of understanding of a patient's overall health ailments as well as the lack of data. For example, a primary care doctor can have limited training and limited experience related to certain health conditions (e.g., mental health). Moreover, health providers employ a subjective decision making process resulting in misdiagnosis as well as suboptimal and delayed treatment plans. Thus, significant challenges exist with respect to health condition diagnosis and treatment, particularly with respect to certain health ailments described above. Moreover, the health provider can provide recommendations which are ineffective and/or undesirable for the patient due to the lack of understanding of the health conditions of the patient, as well as a lack of understanding of recent health care options and associations to potential treatment plans.

The disclosed embodiments provide systems and methods to monitor and gauge patient health in real-time using a dynamically adjustable questionnaire that is electronically presented on a patient device. The disclosed embodiments generate a customized questionnaire for a patient, and transmit the same to the patient device in real-time. For example, the questionnaire can be adjusted in real-time based on previous replies to questions of the questionnaire to dynamically determine whether to include future questions or eliminate questions (e.g., bypass the questions for presentation to the patient). For example, eliminated questions are not transmitted to the patient.

Doing so reduces the number of questions presented to the patient and replies from the patient, which reduces bandwidth consumption since fewer questions and fewer replies are communicated over a network. Moreover, embodiments reduce processing time and resources (e.g., processing power and hardware compute engines to analyze the replies and/or present the replies on a graphical user interface, memory to store the replies and questions, etc.), and encourage patient compliance due to the reduced time and effort to complete the questionnaire. As such, embodiments reduce latency, reduce compute resources and improve patient compliance.

Furthermore, examples at least improve the technical field of automatically generating surveys in real-time and based on prior answers using computer-implemented rules. For example, existing technology can fail to adjust on—the fly and in real-time to user's answers. In detail, existing technology transmits entire surveys to user devices regardless of the answers that a user provides. In some existing technologies, questions can depend from other questions and only be answerable when the other questions have a specific answer. In such existing implementations, all the questions of the questionnaire are transmitted to the user device and are static in nature (e.g., the set of questions comprising the questionnaire does not change). Examples herein dynamically adjust the sets of questions that are transmitted to user devices based on user answers, reducing computing resources, bandwidth, time to process the questionnaire and time to finalize the questionnaire. Further, such examples provide an enhanced questionnaire that is focused, relevant, meaningful and insightful. The answers from such enhanced questionnaires can provide powerful insights into a patient, and be used to identify and initiate impactful questions or treatment plans for the patients.

Some examples further include a machine learning prediction model (e.g., a neural network, generative model, etc.) that is trained based on a large dataset to effectively identify associations between questions, replies and recommendations (e.g., services, online resources, and/or computer applications). For example, the machine learning prediction model can determine and/or generate the most relevant questions for a patient, and can do so based on previous interactions (e.g., previous answers to previous questions) of the patient as well as other features (e.g., personal preferences, social post history, etc.). The most relevant questions can be transmitted to the patient while less relevant questions are bypassed for transmission to the patient.

In some examples, a generative machine-learning model can generate the questions in real-time based on longitudinal patient records. For example, the generative machine-learning model can accept as inputs, previous questions of a questionnaire, answers to the questions by a patient, health data (e.g., medical records) of the patient, historical data of the patient, etc. The generative machine-learning model can generate questions based on the inputs. In some examples, the generative machine-learning model can adjust the phrasing of the questions based on data of the patient. For example, certain demographics (e.g., ages 20-29, 30-39, 40-49, etc.) can be more responsive to questions that are phrased in a certain way. The phrasing of the question can change between different demographics, while the underlying subject matter of the question can remain the same to better obtain a higher level of interest from users to solicit higher quality answers from the users. In some examples, the questions can address specific medical conditions of the patient 102 and as identified from longitudinal patient records.

A machine learning prediction model can further identify recommendations to present to a user based on the patient replies and to mitigate health conditions. In detail, the machine learning prediction model can identify recommendations that are most likely to enhance patient health based on the questions and patient replies to the questions. The machine learning prediction model can further determine that other options (e.g., websites, services, computer applications, etc.) should be bypassed in response to the options being unlikely to enhance the health of the patient. Thus, embodiments can leverage the enhanced abilities of the machine learning prediction model to effectively reduce resource (e.g., computing resources, bandwidth, power, etc.) consumption while enhancing patient outcomes.

In this way, the disclosed embodiments improve the overall process of providing health care and specifically improve the efficiency at which health information is received and analyzed to generate recommendations for health enhancement. Moreover, embodiments herein can implement machine learning to train on sizeable and comprehensive datasets to generate the questionnaires and recommendations. Doing so enables several technical enhancements, including removing human subjectivity from decision making (e.g., diagnosis and treatment) enabling a more consistent approach to questionnaires and recommendations.

Thus, embodiments result in several technical enhancements. By removing human subjectivity, health conditions are accurately assessed. Based on the accurate assessment, early medical interventions (e.g., recommendations) are implemented to minimize patient impact while also reducing computing resources. For example, once a health condition is identified in a patient, recommendations are automatically selected to mitigate the health condition and/or reduce the probability of the health condition occurring.

Moreover, yet another technical enhancement is faster speed and higher efficiency of identification of health conditions and treatment, while also conserving computing resources by automatically, dynamically, and intelligently selecting relevant questions and effective recommendations. Yet another technical enhancement can include using a rigorous, computerized process to perform tasks (e.g., an efficient way to generate a dynamic questionnaire, identify health conditions and generate recommendations based on training data associated with a plurality of patients) that were not previously able to be performed by humans in a practical or accurate manner.

FIG. 1 illustrates a questionnaire generation, analysis and treatment process 100. A healthcare provider device 132, a questionnaire and recommendation platform (QRP) 112 (e.g., a cloud-based, healthcare-related computing system), a patient device 104 (e.g., a user device) and application programming interface (API) 130 are communicatively coupled over a network 106 (e.g., Internet, telephony network, etc.). The API 130 can be software, and can also be part of the QRP 112 and/or patient device 104 in some examples, or separate from the QRP 112 and/or patient device 104 to execute on a different hardware platform.

A patient 102 (e.g., a current patient) has a patient device 104. The patient device 104 can be any type of computing device (e.g., mobile device, desktop computer, tablet, personal digital assistant, etc.). The patient 102 can receive and transmit information to the QRP 112 with the patient device 104 and over the network 106. The API 130 can translate information passed between the QRP 112 and the patient device 104 to facilitate communication therebetween.

The QRP 112 includes hardware (e.g., circuitry, a processor, computing system) and/or software (e.g., at least one non-transitory computer readable storage medium comprising a set of instructions, which when executed by a computing system, cause the computing system to execute the operations described herein, etc.) to execute the operations as described herein. In detail, the QRP 112 dynamically generates questions for a questionnaire for example based on a user request from the patient 102 (e.g., a user), receive replies to the questions and dynamically generates a recommendation 118 based on the replies to the questions. The questions can relate to any health care relevant question, such as mood, physical pain, emotional states, past medical history (PMH), family diseases, social history, weight, heart rate, etc. The QRP 112 can identify the patient 102 based on a user request from the patient device 104 and retrieve patient data to guide the questionnaire process.

The recommendation 118 (e.g., a user suggestion) is transmitted to the patient device 104 which displays content (e.g., on a graphical user interface) of the recommendation 118 (e.g., applications, services, etc.) to address a health condition which may be diagnosed from the answers. A graphical user interface of the patient device 104 displays the content (e.g., services, applications, websites, etc.) of the recommendation 118. The patient 102 can select (e.g., click-through) the services, applications and websites of the recommendation 118 displayed on the patient device 104. In some examples the recommendation 118 can include a lab order, a doctor visit scheduling, lab results, etc.

In detail, a question and recommendation controller (QRC) 136 can access the question database 110 to retrieve questions from the first-N questions. That is, the question database 110 stores first-N questions. The first-N questions can form a questionnaire (e.g., a document that is used to identify health conditions). The questionnaire can be generated based on a new diagnosis of the patient 102, and/or a lack of a medical provider documenting an answer to a question relating to the new diagnosis. The question is part of the standard of care or Subjective, Objective, Assessment and Plan (SOAP).

Not all of the first-N questions are relevant for each patient and/or require an answer from each patient. Thus, the QRC 136 selects a first subset of the questions (e.g., first and second questions) of the first-N questions that require a response by the patient 102, while bypassing a second subset (e.g., third and fourth questions) of the first-N questions. The first subset of questions is transmitted to the patient device 104 to solicit patient replies, while the second subset is not transmitted to the patient device 104.

In order to select the questions, the QRC 136 can access a patient database 108. The patient database 108 can store patient data related to the patient 102. The patient data can be pre-populated and retrieved based on a user request that includes identifying information of the patient 102. That is, the patient data can be identified based on the identifying information.

To reduce the data entry of already known information about the patient 102, embodiments retrieve data (e.g., electronic medical records, health measurements such as blood pressure, height, weight, lab results, ethnicity, age, gender, full name, past names, etc.) of the patient 102 from a database (e.g., a low-latency local database) such as the patient database 108. For example, the QRP 112 can access other systems (e.g., a server and/or computing device) that stores electronic medical records and data, identify whether the medical records and data is relevant (e.g., responsive) to one or more questions of the first-N questions, and store the data (if identified as relevant) into the patient database 108. The QRP 112 therefore does not need to transmit the one or more questions to the patient 102 since the answers to the one or more questions have already been obtained and stored in the patient database 108, and thus also avoids receiving replies from the patient 102 for the one or more questions to reduce bandwidth, latency and processing power.

Thus, some of the answers to the first-N questions can be pre-populated with the relevant data. For example, suppose that one question of the first-N questions requests the weight of the patient 102 (e.g., what is the exact weight) and is identified as being relevant for a medical diagnosis. Suppose further that the patient database 108 stores the weight of the patient 102. The one question can be bypassed and not transmitted and/or presented to the patient 102 (the user is not asked the one question) and the answer is rather pre-populated from the weight stored in the patient database 108. Thus, the QRC 136 can determine whether a respective question of the first-N questions has a corresponding answer in the patient database 108, and bypass the respective question if so.

In some examples, the patient database 108 (e.g., data items related to a questionnaire) can be pre-populated from external databases 138. The external databases 138 can be under the direct control of third-parties, and include data related to the patient 102. For example, questionnaire responses can be pre-populated based on structured data capture specifications. Examples can support pre-population of answers to questions as the questionnaire is being provided to the patient, or prior to the questionnaire being provided to the patient 102. For example, as questions of the questionnaire (e.g., the first subset of the first-N questions) are identified and/or generated on the—fly and in real-time (e.g., specific questions that are generated and/or selected for inclusion in the questionnaire based on previous answers to questions), some examples can analyze the external databases 138 for answers to the questions, store the answers to the questions in the patient database 108 and avoids providing the questions to the patient 102.

In some examples, if the QRP 112 determines that several questions will be part of a questionnaire, the QRP 112 can analyze the external databases 138 for answers to the questions, store answers to the questions in the patient database 108 and avoid providing the questions to the patient 102. In some examples, the QRP 112 can access an API to retrieve data to access the external databases 138. Pseudocode I below is an exemplary code to trigger pre-population:

Pseudocode I

```
{
    "resourceType": "Questionnaire",
    "status": "draft",
    "extension": [
        {
            "extension": [
                {
                    "url": "name",
                    "valueId": "patient"
                },
                {
                    "url": "type",
                    "valueCode": "digital-profile"
                },
                {
                    "url": "description",
                    "valueString": "Patient that is the subject of this
                    questionnaire"
                }
            }
        }
```

-continued

Pseudocode I

```
        ],
        "url":"http://.../StructureDefinition/sdc-questionnaire-launchContext"
        }
    ]
```

In pseudocode I, the extensions "url=name" and "'valueId='patient'" is the variable that will be used to extract the data in the resource. "valueId" can adopt different values. The extensions "url=type" and "valueCode='digital-profile'" can be the type of resource that will fetch the data. For example, "digital-profile" can utilizes a Digital Team User Profile API, and "person-record-hub" can utilize a Person Record Hub API.

In some examples, pre-population of answers is a multi-step process. For example, after a questionnaire definition (e.g., answer to a question) is set for pre-population, a following step can be to define a corresponding question item to initiate an initial value. Each question item can contain a questionnaire-initial expression extension to trigger the QRP 112 and particularly the QRC 136 to obtain the initial answer from the patient database 108 based on the expression set on the questionnaire-initial expression extension.

For example, there can be a birthdate question related to the user date of birth. The user date of birth can be found in a patient resource database of the external databases 138. The following Pseudocode II can describe the retrieval of the user data of birth.

Pseudocode II

```
{
    "resourceType": "Questionnaire",
    "status": "draft",
    "extension": [
        {
            "extension": [
                {
                    "url": "name",
                    "valueId": "patient"
                },
                {
                    "url": "type",
                    "valueCode": "digital-profile"
                },
                {
                    "url": "description",
                    "valueString": "Patient that is the subject of this
                    questionnaire"
                }
            ],
            "url": "http:/.../StructureDefinition/sdc-questionnaire-launchContext"
        }
    ],
    "item": [
        {
            "extension": [
                {
                    "url": "http://.../StructureDefinition/sdc-questionnaire-
                    initialExpression",
                    "valueExpression": {
                    "language": "text/fhirpath",
                    "expression": "%patient.birthDate"
                }
            }
        ],
        "linkId": "patient-birthdate",
        "text": "Date of birth",
        "type": "date"
        }
    ]
}
```

In pseudocode II, "'till': 'http:// . . . /StructureDefinition/ sdc-questionnaire-initialExpression'," is a constant value. Further, in pseudocode II, the value expression "language: text/fhirpath" is a language that has a constant value: "text/ fhirpath." Further, the value expression "expression: % patient.birthDate" is the expression to calculate. In this example, embodiments will obtain patient.birthData from the Patient Resource of the external databases 138. The patient birth data maps to the patient valueId and the type is mapped to digital-profile.

After the birthdate question is identified as being a pre-population candidate, examples can then set a placeholder value indicating that the birthdate question is to be pre-populated. The placeholder value can be associated with the birthdate question. When a survey is generated that includes the birthdate question, the QRP 112 and/or QRC 136 may identify that the placeholder value is stored in association with the birthdate question, and determine that the answer to the birthdate question is to be retrieved from the external databases 138 and/or patient database 108. The answer can then be stored in association with the birthdate question (e.g., replaces the placeholder value) and bypasses presenting the birthdate question to the patient 102. Thus, the QRP 112 and/or QRC 136 may retrieve the answer to the birthdate question without ever presenting the birthdate question to the patient 102.

Marking the birthdate question with the placeholder value enables up-to date information to be retrieved from the external database 138. For example, suppose that the answer can be changed in real-time (e.g., blood pressure, weight, etc.). Retrieving the answer too early can result in inaccuracies. Thus, a placeholder value can be stored simply to mark that the answer is retrievable from the external databases 138. The answer may then be retrieved at a later time to ensure that the answer is the most-up to date value for the answer. Furthermore, if the QRP 112 and/or QRC 136 is unable to obtain the answer, the QRP 112 and/or QRC 136 may not return an error, but will instead present the birthdate question to the patient 102 and request that the patient 102 provide an answer to the birthdate question.

The following pseudocode III represents the client asking for the first question (e.g., a birthday question) on a questionnaire:

```
                        Pseudocode III

{
        "resourceType": "QuestionnaireResponse",
        "contained": [
        {
            "resourceType": "Questionnaire",
            "id": "welcome",
            "item": [
            ]
        }
        ],
        "status": "in-progress",
        "questionnaire": "#welcome
    }
```

The following pseudocode IV represents the response containing the definition of the birthdate question and the prepopulated data. Pseudocode IV can be executed by the QRP 112:

```
                        Pseudocode IV

{
        "resourceType": "QuestionnaireResponse",
        "contained": [
            {
            "resourceType": "Questionnaire",
            "id": "welcome",
            "item": [
                {
                "linkId": "personalInfo",
                "prefix": "1",
                "text": "Review your information",
                "type": "group",
                "item": [
                    {
                        "linkId": "fullname",
                        "text": "Full Name",
                        "type": "string"
                    }
                ]
                }
            ]
            }
        ],
        "item": [
            {
            "linkId": "personalInfo",
            "item": [
                {
                "linkId": "fullname",
                "answer": [
                    {
                        "valueString": "Jennifer Smith"
                    }
                ]
                }
            ]
            }
        ],
        "id": "xyz",
        "status": "in-progress"
    }
```

The QRC 136 can operate in several different modes to select questions of the first-N questions for presentation to the patient 102, and an order to present the selected questions. In detail, the QRC 136 includes a linear adaptive flow controller 120, a rule adaptive flow controller 122, a graph adaptive flow controller 124 and a non-adaptive flow controller 126.

The linear adaptive flow controller 120 selects one question of the first-N questions at a time in a linear order defined by a question order, while bypassing some of the questions. The linear adaptive flow controller 120 adapts questions (e.g., an order, bypasses questions, etc.) based on previous responses (replies to other questions) of the patient 102.

The rule adaptive flow controller 122 selects one question of the first-N questions at a time, in an order defined by a rules engine of the rule adaptive flow controller 122 (questions are selected in an order that does not conform to the question order). The rule adaptive flow controller 122 can have a state machine flow to adapt questions (e.g., an order, bypasses questions, etc.) based on previous responses (replies to other questions) of the patient 102. The rule adaptive flow controller 122 includes a series of rules that define which questions of the first-N questions to select, the order of presentation and different topics. The order of presentation can mean an order of the selected questions to be transmitted and shown to patient 102 on patient device 104 (e.g., the N question can be presented prior to the first question).

In some examples the rule adaptive flow controller 122 includes a state machine that executes when the patient 102 provides a reply to a respective question of the first-N questions. As one example, suppose that the respective question is "are you a woman," and the reply is "Yes—I am a woman." The following question can be selected specifically based on the reply to the respective question, and could be "are you pregnant" (i.e., a condition which can only occur to women and is therefore only asked to women). If however, the reply above was "No—I am a man," the question relating to pregnancy would not be selected or presented to the patient 102 since question relating to pregnancy is irrelevant to men. As another example, one of the states could indicate whether to show a next question or not, or generate another set of rules (e.g., generate the recommendation).

In some examples, the rule adaptive flow controller 122 can further generate a recommendation 118 for the patient 102. For example, the rule adaptive flow controller 122 can establish a weight for each reply received from the patient 102 based on a rating of importance of corresponding questions. Each of the replies is translated into a score based on the weights, and a total score is calculated based on a summation of all scores of the replies. The total score can be indicative of different content for the recommendation 118. For example, different thresholds (e.g., score boundaries) can be established for different content. If the total score falls between a first threshold and a second threshold, first content (e.g., websites, services, computer applications) can be recommended to the patient 102 as recommendation 118. If the total score falls between the second threshold and a third threshold, second content (e.g., websites, services, computer applications) can be recommended to the patient 102 as recommendation 118.

An exemplary score can be defined as follows:

$$score = \sum_{i=1}^{N} w_i y \qquad \text{Equation 1}$$

In Equation 1, N is the number of questions, y is the answer to a question and w is the weight for the question. For example, a simple questionnaire can have two questions and the following weightings for answers to the two questions:

TABLE I

| Answer | Weight |
|--------|--------|
| Good | 0 |
| Fair | 1 |
| Poor | 2 |

The weights can be decimal values in some examples. An extension can define the weight value. The example below shows how the extension can be defined:

Pseudocode V

```
{
    "extension": [
    {
        "url": "http://... /StructureDefinition/ordinalValue",
        "valueDecimal": 0
    }],
    "valueString": "good"
}
```

The question definitions can be as follows:

TABLE II

| Text | Possible Answers |
|------|------------------|
| Over the past week, how would you rate your mood, concentration, and overall well-being? | good, fair, poor |
| Over the past week, how have you been managing your emotions of nervousness, anxiety, or feeling on edge? | good, fair, poor |

The following Table III can provide the answers to the questions from the patient 102:

TABLE III

| Text | Possible Answers |
|------|------------------|
| Over the past week, how would you rate your mood, concentration, and overall well-being? | good |
| Over the past week, how have you been managing your emotions of nervousness, anxiety, or feeling on edge? | poor |

The score calculation can be then executed as follows based on Equation 1. The score would be score=(good)*(0)+(poor)*(2)=2.

Following the example discussed above, pseudocode for the question can be defined as follows:

Pseudocode VI

```
{
    "linkId": "wellbeing.assessment.emotions",
    "prefix": "005",
    "text": "Over the past week, how have you been managing your emotions of
nervousness, anxiety, or feeling on edge?",
    "type": "choice",
    "answerOption": [
    {
        "extension": [
        {
            "url": "http://.../ StructureDefinition/ordinalValue",
            "valueDecimal": 0
        }
    ],
```

-continued

```
                        Pseudocode VI

"valueString": "good"
   },
   {
    "extension": [
        {
           "url": "http://.../StructureDefinition/ordinalValue",
           "valueDecimal": 2
        }
      ],
      "valueString": "poor"
     }
   ]
}
```

After the question answer weights are defined in the questionnaire, examples can define a question item that would capture the actual score. This question item can be part of the definition of the scoring process. The question item can have "variables" and an "equation." Variables hold temporary values and the equation can be the mathematical representation of the algorithm. Examples of variables can be provided as follows:

TABLE IV

| Variables | Purpose |
|---|---|
| $Q(n) = Q(a) * Q(w)$ where $Q(a)$ = answer of the question and $Q(w)$ is the weight | Temporary holds the weight calculation for a specific answer |
| $Q(y) = Q(a)$ equals 'terrible' | If a particular answer contains a specific value this variables holds the value of "true" otherwise "false" |

An extension to define a variable in the questionnaire item can further be defined. The extension contains an object (e.g., named valueExpression) that can be defined as follows:

TABLE V

| Key | Description | Optional/Required |
|---|---|---|
| Name | The name of the variable | Required |
| Language | The scripting language | Required |
| Expression | The algorithm expression. The expression can be conformant with the Application Path specification | Required |

A pseudocode example is shown below.

```
                        Pseudocode VII

{
   "url": "http://.../StructureDefinition/variable",
   "valueExpression": {
      "name": "q1_value",
      "language": "text/fhirpath",
      "expression": "%questionnaire.item.where(linkId =
      'wellbeing.assessment.mood').answerOption.where
      (valueString=%resource.item.where(linkId=
      'wellbeing.assessment.mood').answer.valueString).extension.where
      (url=%scoreExt).valueDecimal"
   }
}
```

The variable name in the above case is "q1_value", the expression can be a Fast Healthcare Interoperability Resources (FHIR) Path expression utilizing a "where" clause that can be flexibly defined. The expression obtains the questionnaire definition for the question with linkId (unique id) equals to "wellbeing.assessment.mood" and obtains the decimal value from the extension defined in the variable "scoreExt." Expressions can reference other variables by appending % before the name of the expressions.

Some definitions (e.g., questionnaire which is utilized to reference the Questionnaire definition, and resource which is utilized to refer to the FHIR resource being evaluated) can be reserved. An example of a calculated expression can be provided below in Pseudocode VII:

```
                        Pseudocode VIII

{
"url":"http://... /StructureDefinition/sdc-questionnaire-calculatedExpression",
"valueExpression": {
"description": "Total score calculation",
"language": "text/fhirpath",
"expression": "iif(%any_questions_answered, iif(%q1_value.exists( ), %q1_value,
0) + iif(%q2_value.exists( ),
%q2_value, 0), 0), { })"
   }
}
```

In the above, the extension (e.g., "url":"http:// . . . /Struc-tureDefinition/sdc-questionnaire-calculatedExpression") can contain the following values:

TABLE VI

| Key | Description | Optional/Required |
|-----|-------------|-------------------|
| description | A brief description of the equation | Required |
| language | The scripting language (e.g., supports text/fhirpath) | Required |
| expression | The algorithm expression. The expression can be conformant with a predefined (e.g., FHIR) specification | Required |
| name | Puts the result of the calculation in the variable context. This value is only needed if the calculation is reference by another "calculation". | Optional |

The graph adaptive flow controller 124 can select one question of the first-N questions at a time, in an order defined by node relationships of a graph which maps relationships. The graph adaptive flow controller 124 adapts questions (e.g., an order, bypasses questions, etc.) based on previous responses (replies to other questions) of the patient 102. The graph adaptive flow controller 124 can have a schema that describes a flow of a graph representation.

Notably, each of the linear adaptive flow controller 120, the rule adaptive flow controller 122 and the graph adaptive flow controller 124 can bypass one or more of the first-N questions where the one or more questions are never transmitted to the patient device 104, and dynamically adjust an order to present selected questions of the first-N questions. Furthermore, the linear adaptive flow controller 120, the rule adaptive flow controller 122 and the graph adaptive flow controller 124 can cause a variable number of questions to be presented at any one time on the patient device 104 (e.g., on a user interface).

The non-adaptive flow controller 126 does not bypass any questions and rather provides all of the first-N questions to the patient device 104 in the question order. Regardless of the mode, selected questions are provided to the patient 102 via the patient device 104 (e.g., presented on a graphical user interface) and the patient 102 can provide a reply to the selected questions via the patient device 104. In some examples, the QRC 136 can toggle between selecting questions with the linear adaptive flow controller 120, the rule adaptive flow controller 122, the graph adaptive flow controller 124 and the non-adaptive flow controller 126. In some examples, one or more of the linear adaptive flow controller 120, rule adaptive flow controller 122, graph adaptive flow controller 124 and non-adaptive flow controller 126 can generate the recommendation 118.

In some examples, the machine learning question and recommendation model (MLQRM) 116 (e.g., generative AI) can identify which questions to propose to the patient 102. For example, the MLQRM 116 can determine, based on answers and the pre-populated patient data of the patient database 108, which questions to select from the question database 110. In doing so, the MLQRM 116 can determine which questions of the first-N questions are most likely to be relevant in diagnosing the patient 102. In some examples, the MLQRM 116 can be trained on data (e.g., answers and selected questions) associated with the linear adaptive flow controller 120, the rule adaptive flow controller 122, the graph adaptive flow controller 124 and/or the non-adaptive flow controller 126. In some examples, the MLQRM 116 can be trained based on historical data from a historical database 134. The historical database 134 can include historical data (questions and answers) associated with a plurality of patients. This will be explained further below.

In this example, the QRP 112 receives a patient request for a questionnaire from the patient device 104, where the questionnaire is associated with the first-N questions stored in the question database 110. The QRC 136 accesses the question database 110 to select the first question from the first-N questions for example with an adaptive flow controller of the linear adaptive flow controller 120, rule adaptive flow controller 122 and graph adaptive flow controller 124. The QRP 112 transmits the first question to the patient device 104 via the API 130. The patient device 104 displays the first question. The patient 102 can provide a first patient reply to the first question through the patient device 104 and the API 130. The QRP 112 receives the first patient reply. The QRC 136 accesses the question database 110 to select a second question from the first-N questions based on the first patient reply, for example with an adaptive flow controller of the linear adaptive flow controller 120, rule adaptive flow controller 122 and graph adaptive flow controller 124. The QRP 112 transmits the second question to the patient device 104 via the API 130. The second question can be displayed on the patient device 104. The patient 102 can provide a second patient reply to the second question via the patient device 104. The second patient reply can be transmitted to the QRP 112 via the API 130. The QRP 112 receives the second patient reply.

The first and second patient replies are stored in association with the first and second questions in a reply associations database 114. The reply associations database 114 can store all questions proposed to the patient 102, and all replies that are provided in response to the questions. In this example, two questions and two patient replies are provided, but it will be understood that any number of questions and patient replies can be included within embodiments herein.

The first and second patient replies can be mapped to the first and second observations 140, 142. Observations, including the first and second observations 140, 142, can be used in healthcare environments, and support diagnosis, progress monitoring, baseline determinations and patterns, capture demographic characteristics, as well as capture results of tests performed on products and substances. Observations can take different forms (e.g., name/value pair assertions with some metadata). Thus, an observation can be a concept that is used to extract and describe data for the patient 102 (e.g., qualitative data). Data can be classified as vital signs (e.g., weight, height, blood pressure, etc.), assessment score, and so forth.

Examples support the delivery of questionnaires and responses (e.g., first and second patient replies) processing known as a questionnaire response. For example, a questionnaire can contain questions called items. Items can contain mapping information on how the items can be mapped to observations. Each respective observation has a code data item. The code data item describes the respective observation. Several pre-defined code data items may be provided and/or contained in each observation. To link an item (e.g., a question) to an observation, examples map to the observation code (e.g., code data item). Examples can signal that an observation can be extracted from the questionnaire item based on an extension. The following pseudo-code is an example of a questionnaire that contains an item to be extracted as an observation.

Pseudocode IX

```
{
   "description": "Initial survey for the d14e patient app for behavioral health",
   "item": [
       {
          "text": "Which is your current weight",
          "type": "quantity",
          "linkId": "en_questionnaire_weight",
          "extension": [
              {
                 "url": "http://.../StructureDefinition/questionnaire-unit",
                 "valueCoding": {
                 "system": "http://unitsofmeasure.org",
                 "code": "[lb_av]",
                 "display": "pound"
                 }
              },
              {
                 "url":                       "http://.../StructureDefinition/sdc-questionnaire-
                 observationLinkPeriod",
                 "valueDuration": {
                    "value": 1,
                    "unit": "years",
                    "system": "http://unitsofmeasure.org",
                    "code": "a"
                 }
              }
          ],
          "required": true,
          "code": [
              {
                 "system": "http://loinc.org",
                 "code": "29463-7"
              }
          ]
       }
   ],
   "name": "d14eSurvey",
   "resourceType": "Questionnaire",
   "subjectType": [
       "Patient"
   ],
   "status": "draft",
   "title": "Initial behavioral health survey",
   "url": "https://.../01G3Y2QCGM0XHS93SETBBE74VP",
   "version": "1",
   "meta": {
       "tag": [
           {
              "code": "d14eonboardingv2",
              "display": "d14eonboardingv2",
              "system":"https://.../valueset-questionnaire-category"
           }
       ]
   },
   "extension": [
       {
          "url": "http://.../StructureDefinition/designNote",
          "valueMarkdown": "source.text.cdn"
       }
   ]
}
```

In the above questionnaire of pseudocode IX, there is an item (question) that requests the weight of the patient 102. This question has an extension that defines an observation link period (this measurement can either update or create a new observation based on this period). The item also contains a code that maps to a predefined observation type. Thus, based on the above, the first patient reply is mapped to the first observation 140, and the second patient reply is mapped to the second observation 142. The first and second observations 140, 142 can quantify the first and second patient replies, and/or represent the first and second patient replies in a standard format that is efficiently analyzed by the QRC 136.

As noted above, in some examples, the QRC 136 can retrieve patient information associated with the patient 102 from the patient database 108. The patient information includes one or more of identifying information of the patient 102 and/or health measurements (e.g., a blood pressure, resting heart rate, weight, etc.) of the patient 102. The QRC 136 determines whether to select a third question of the first-N questions for transmission to the patient device 104 based on whether an answer to the third question is contained within the patient information. If the answer is contained in the patient information, the third question is bypassed to reduce consumption of computing resources and bandwidth. If the answer is not contained, the third question is transmitted to the patient device 104.

The MLQRM 116 can generate the recommendation 118 rather than the linear adaptive flow controller 120, rule adaptive flow controller 122, graph adaptive flow controller 124 and non-adaptive flow controller 126. The MLQRM 116 can generate the recommendation 118 based on the association data in the reply associations database 114. For example, the QRC 136 can determine the recommendation 118 based on the first question being associated with the first patient reply, and the second question being associated with the second patient reply. In detail, the MLQRM 116 can determine the recommendation 118 based on the first and second patient replies, and cause the recommendation 118 to be transmitted to the patient device 104.

The associations between the first and second questions, the first and second patient replies and the first and second observations 140, 142 can be indicative of an underlying health condition (e.g., depression, anxiety, fatigue, body pain, etc.). Thus, the MLQRM 116 can identify the health condition and generate the recommendation 118 to include treatment options (e.g., first recommended service, a first application, and a first website) to mitigate and/or prevent the health condition. In some examples, the MLQRM 116 does not necessarily have to identify the health condition, and can determine the recommendation 118 based on inputs (the associations between questions and answers).

In some examples, the MLQRM 116 can generate a series of recommendation vectors to represent different recommendations. For example, the recommendations can be mapped to a multi-dimensional vector space in the form of vectors referred to as recommendation vectors. The MLQRM 116 generates a patient vector based on the first and second patient replies and/or the first and second observations 140, 142. In particular the patient vector can be based on the first question being associated with the first patient reply and/or the first observation 140, and the second question being associated with the second patient reply and/or the second observation 142. The MLQRM 116 calculates differences between the recommendation vectors and the patient vector, and selects content for the recommendation 118 based on the differences.

In some examples, the MLQRM 116 selects a selected recommendation vector of the recommendation vectors associated with the lowest difference from the differences for the recommendation 118. In some examples, the differences can be distances that are computed in the multi-dimensional space. For example, a lower distance between two vectors indicates a strong similarity between the two vectors, while a larger distance between the two vectors indicates a weak similarity (or a dissimilarity) between the two vectors. The distance can be a Euclidean Distance, a Manhattan Distance, a Minkowski Distance, a Hamming Distance etc. Recommendations corresponding to recommendation vectors with low distances from the patient vector (e.g., distance below a threshold) can be selected to form the recommendation 118, while other recommendations associated with larger distances can be bypassed and do not form part of the recommendation 118. The selected recommendation corresponds to and/or represents the recommendation 118.

The recommendation 118 can correspond to a different service, application, program, website, etc. that can mitigate a health condition of the patient 102. For example, if the patient 102 has anxiety, the recommendation 118 can include a first recommendation for an application for meditation, a second recommendation for a therapy application, a third recommendation for a recommended health provider that specializes in anxiety, a fourth recommendation for an anxiety support website, etc. Notably, the patient 102 can be unaware that they have anxiety. Rather, first-N questions can include content to detect whether a patient has anxiety (e.g., "on a scale of 1-10, how uncomfortable are you in public settings?") without directly asking the patient to diagnose themselves (e.g., "do you have anxiety?"). In doing so, accurate detection of health conditions is facilitated since often times patients are unable to accurately diagnose themselves.

In some examples, the MLQRM 116 can also select the content of the recommendation 118 based on implicit and explicit feedback associated with the patient 102. For example, the QRC 136 can access the patient database 108 to retrieve patient data, where the patient data includes implicit feedback associated with the patient 102 and explicit feedback associated with the patient 102. The MLQRM 116 can generate the recommendation 118 based on the implicit and the explicit feedback.

The explicit feedback includes one or more of social network data (e.g., data from any social website such as friends, likes, dislikes, comments, etc.) associated with the patient 102, personal preferences (e.g., reviews and/or ratings associated with merchandise and/or stores), and recommendation button interactions (e.g., recommended services, website buttons, etc.) associated with the patient 102. The implicit feedback includes one or more of purchase history associated with the patient 102, potential shopping items of the patient 102, and musical preferences of the patient 102. In some examples, the MLQRM 116 can generate the patient vector described above based on the implicit and explicit feedback. Thus, some examples can identify preferences of the patient 102 based on patient data (e.g., historical interactions of the patient tracked across a plurality of computing platforms and servers) to determine appropriate and the most effective (e.g., utilization rate as measured by click-through or how frequently a service, website or application is accessed) recommendation 118 for the patient 102.

In some examples, the patient data can also include other identifying data of the patient 102, such as demographic information of the patient 102, health measurements of the patient 102 (e.g., blood pressure, weight, family history, etc.) and other information (e.g., distinct from the questionnaire) of the patient 102. The MLQRM 116 can generate the recommendation 118 based on the demographic information, health measurements and the other information.

In order to train the MLQRM 116, some embodiments access the historical database 134. The QRP 112 can gather training data that includes a plurality of patient responses provided by a plurality of patients, and engagement data identifying how the plurality of patients have engaged with a plurality of recommendations. The MLQRM 116 translates the plurality of patient responses and the plurality of recommendations into recommendation effectiveness scores, and maps the recommendation effectiveness scores into a vector space to generate the recommendation vectors. The recommendation effectiveness scores can quantity an effectiveness of the plurality of recommendations. For example, the recommendation effectiveness scores can be metrics indicating whether the patients associated with certain responses interacted (e.g., as measured by click-throughs, interactions, time spent with content, etc.) with recommendations that were provided to the patients based on the certain responses. For example, suppose that four different recommendations were provided to a first patient based on responses of the first patient to questions. Recommendation effectiveness scores can be generated for each of the four different recommendations based on how the patient interacted with the four different interactions.

In some examples, the training data is immediately fed into the MLQRM 116 without storage into the historical database 134. In some examples, the QRC 136 can generate recommendations based on static rules and via a graph database engine of the graph adaptive flow controller 124. The recommendations of the graph adaptive flow controller 124 can be presented to a patient to identify effectiveness (e.g., click-throughs, interaction, etc.) of the recommendations. The MLQRM 116 can generate recommendations and/or be trained based on the recommendation vectors and in parallel with execution of the graph adaptive flow controller 124. The MLQRM 116 can track effectiveness of the recommendations generated by the graph adaptive flow controller 124 (e.g., click through rates) and determine whether one or more recommendations of the MLQRM 116 correspond to any of the recommendations of the graph adaptive flow controller 124. If the one or more recommendations correspond to a recommendation of the graph adaptive flow controller 124, a loss can be generated based on the measured effectiveness of the recommendation of the graph adaptive flow controller 124. The MLQRM 116 can be updated based on the loss (e.g., adjust the recommendation vectors and/or how patient vectors are generated).

In some examples, all communications comply with the Fast Healthcare Interoperability Resources (FIHR) standard which is a standard for health care data exchange. FIHR defines security and privacy standards, conformance and terminologies.

For example, the QRP 112 includes a security controller 128 that executes FIHR security measures, including an authentication process (e.g., two-factor authentication, challenge questions, login, etc.) on the patient 102 to authenticate the patient 102 and verify the identity of the patient 102. The security controller 128 can then determine that communication with the patient 102 is to be executed in response to the patient 102 being authenticated and permit the QRP 112 to communicate first and second questions to the patient device 104. The authentication process can be executed with the patient device 104.

The security controller 128 can further encrypt the first question, the second question, and the recommendation 118 prior to transmission to the patient device 104. The patient device 104 can decrypt the first question, the second question, and the recommendation 118 with a shared key that is shared by the security controller 128 and the patient device 104. In some examples, the security controller 128 encrypts data with a public key, while the patient device 104 can decrypt data with a private key. Similarly, the patient device 104 can encrypt the first patient reply and second patient reply (e.g., via a public-private key system or a shared key) and the security controller 128 can decrypt the first and second patient replies. In some examples the first question, second question, first patient reply and second patient reply are encrypted while at rest in the reply association database 114, and only decrypted when in use.

In some examples, the MLQRM 116 is a Restricted Boltzmann Machine mixed with a convolutional neural network (e.g., a 2 layer network). In some examples the MLQRM 116 is a reinforcement learning architecture. In some embodiments, the QRC 136 can include a statistical engine to execute statistical modelling and execute question and recommendation processes as described herein.

Thus, embodiments can readily identify health conditions based on a focused and efficient questionnaire that consumes reduced processing power, bandwidth and resources. Moreover, embodiments can provide effective recommendations that include focused guidance and advice for the patient 102.

In some examples, the MLQRM 116 can operate and be trained in parallel to execution of the linear adaptive flow controller 120, the rule adaptive flow controller 122, the graph adaptive flow controller 124 and/or the non-adaptive flow controller 126. The linear adaptive flow controller 120, the rule adaptive flow controller 122, the graph adaptive flow controller 124 and/or the non-adaptive flow controller 126 can select questions of the first-N questions and the QRC 136 can track the replies to the selected questions. The MLQRM 116 can be a neural network that is trained based on the tracked replies and the questions, as we as the effectiveness of any proposed recommendations based on the same. In some examples, the healthcare provider device 132 can also receive the recommendation 118.

The network 106 can include, or operate in conjunction with, an ad hoc network, an intranet, an extranet, a virtual private network (VPN), a local area network (LAN), a wireless network, a low energy Bluetooth (BLE) connection, a WiFi direct connection, a wireless LAN (WLAN), a wide area network (WAN), a wireless WAN (WWAN), a metropolitan area network (MAN), the Internet, a portion of the Internet, a portion of the Public Switched Telephone Network (PSTN), a plain old telephone service (POTS) network, a cellular telephone network, a wireless network, a Wi-Fi® network, another type of network, or a combination of two or more such networks. For example, a network or a portion of a network can include a wireless or cellular network and the coupling can be a Code Division Multiple Access (CDMA) connection, a Global System for Mobile communications (GSM) connection, or other type of cellular or wireless coupling. In this example, the coupling can implement any of a variety of types of data transfer technology, such as Single Carrier Radio Transmission Technology (1×RTT), Evolution-Data Optimized (EVDO) technology, General Packet Radio Service (GPRS) technology, Enhanced Data rates for GSM Evolution (EDGE) technology, third Generation Partnership Project (3GPP) including 3G, fourth generation wireless (4G) networks, fifth generation wireless (5G) networks, Universal Mobile Telecommunications System (UMTS), High Speed Packet Access (HSPA), Worldwide Interoperability for Microwave Access (WiMAX), Long Term Evolution (LTE) standard, others defined by various standard setting organizations, other long range protocols, or other data transfer technology.

The MLQRM 116 trains one or more machine learning techniques based on the sets of input-output pairs of paired training data sets in some examples. For example, the MLQRM 116 can train the machine learning (ML) model parameters of the MLQRM 116 by minimizing a loss function based on one or more ground-truth types to generate recommendations based on answer-question associations. The ML model can include any one or combination of classifiers or neural networks, such as an artificial neural network, a convolutional neural network, an adversarial network, a generative adversarial network, a deep feed forward network, a radial basis network, a recurrent neural network, a long/short term memory network, a gated recurrent unit, an auto encoder, a variational autoencoder, a denoising autoencoder, a sparse autoencoder, a Markov chain, a Hopfield network, a Boltzmann machine, a restricted Boltzmann machine, a deep belief network, a deep convolutional network, a deconvolutional network, a deep convolutional inverse graphics network, a liquid state machine, an extreme learning machine, an echo state network, a deep residual network, a Kohonen network, a support vector machine, a neural Turing machine, and the like.

Figure 2:
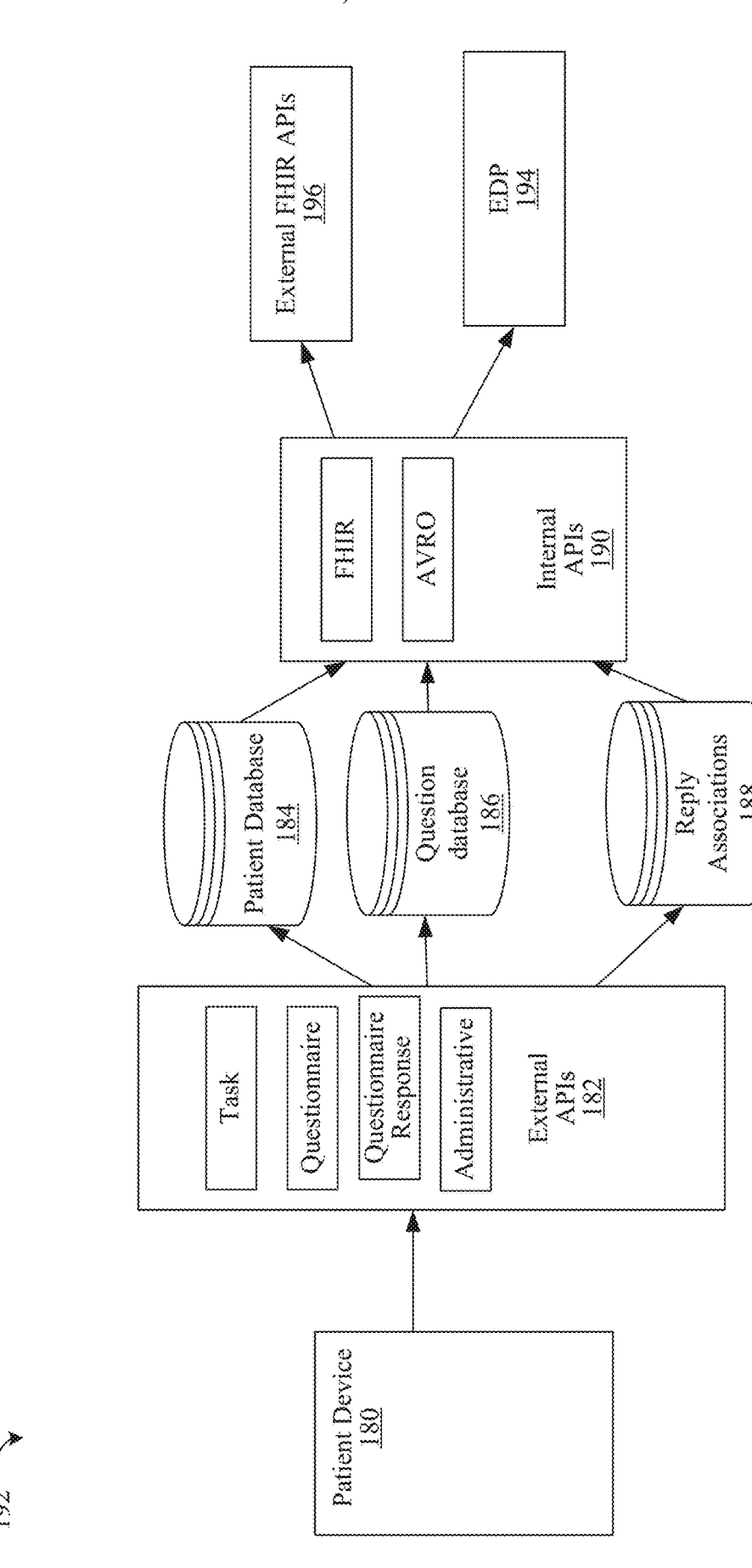
FIG. 2 is a block diagram of an example of a questionnaire and recommendation architecture according to an embodiment.

FIG. 2 illustrates a questionnaire and recommendation architecture 192. Aspects of the questionnaire and recommendation architecture 192 can readily be substituted for and/or form a part of the QRP 112 (FIG. 1). The architecture 192 includes a patient device 180 that communicates with a series of external APIs 182. The external APIs 182 include a task API, a questionnaire API that provides new questions to the patient device 180, a questionnaire response API which provides patient replies to one or more of the question database 186 and the reply associations database 188, and an administrative API that can provide data to the patient database 184. Internal APIs 190 are for configuration and/or compliance with one or more standards such as FIHR. Enterprise Data Platform (EDP) 194 can interact with databases through the internal APIs 190. External FHIR APIs 196 (e.g., externally exposed FHIR APIs) can connect to EHR (Electronic Health Record) systems through the internal APIs 190.

Figure 3:
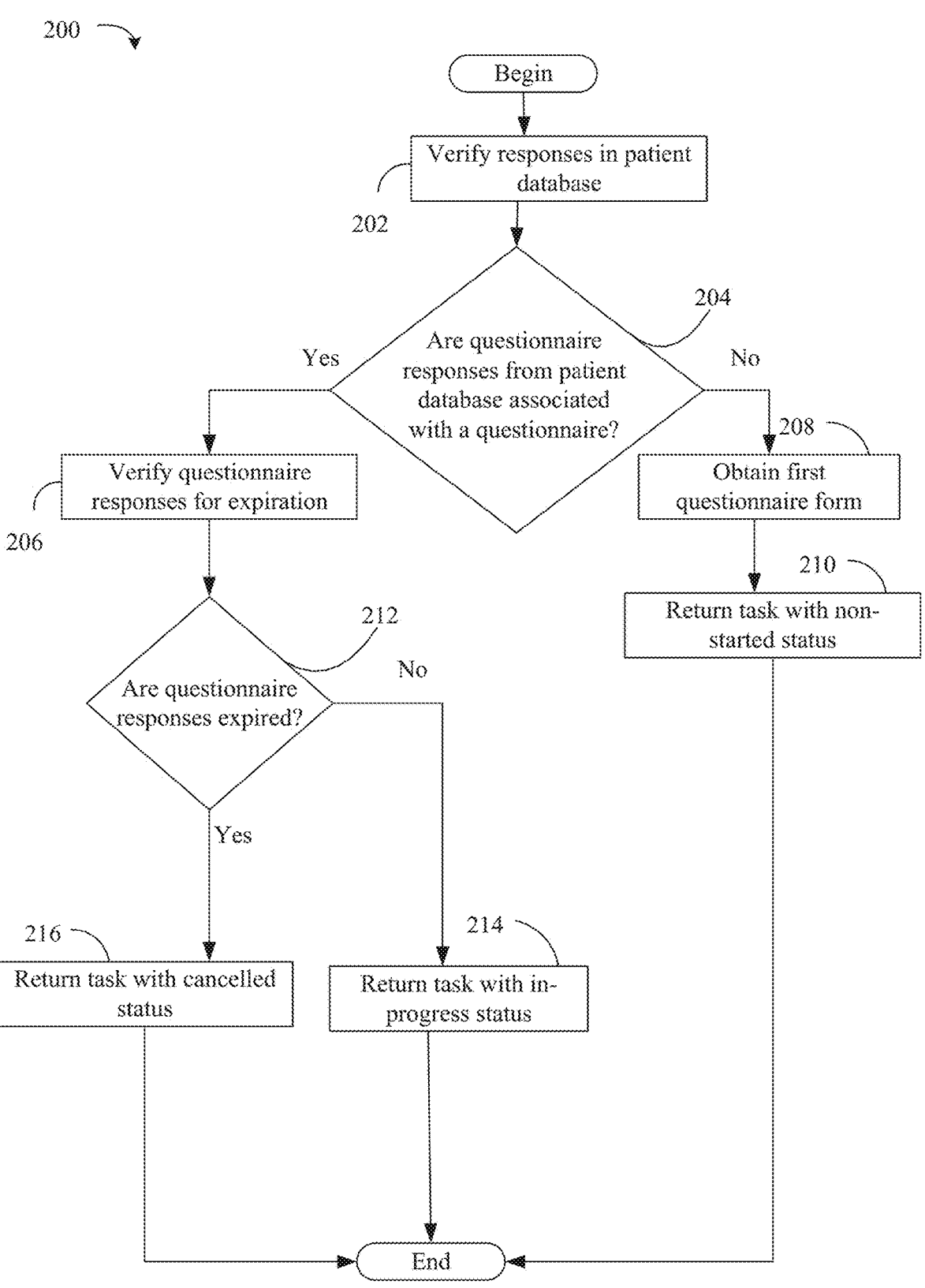
FIG. 3 is a flowchart of an example of a method of determining whether questions are to be provided to a patient or bypassed based on patient data according to an embodiment.

FIG. 3 illustrates a method 200 of determining whether questions are to be provided to a patient or bypassed based on patient data. The method 200 can generally be implemented in conjunction with any of the embodiments described herein, for example the questionnaire generation, analysis and treatment process 100 (FIG. 1), and/or questionnaire and recommendation architecture 192 (FIG. 2). In an embodiment, the method 200 is implemented in logic instructions (e.g., software), configurable logic, fixed-functionality hardware logic, computer readable instructions stored on at least one non-transitory computer readable storage medium that are executable to implement method 200, circuitry, etc., or any combination thereof.

Illustrated processing block 202 verifies responses in a patient database. Illustrated processing block 204 determines if questionnaire responses (e.g., answers) from the patient database are associated with a questionnaire. That is, processing block 204 determines if answers to questions in the questionnaire are stored in the patient database. The questionnaire responses can pertain to a particular patient. If the questionnaire responses are associated with the questionnaire, illustrated processing block 206 verifies the questionnaire responses for expiration. For example, certain health measurements (e.g., weight, blood pressure, vision power, etc.) can only be relied upon for a certain period of time due to the normal fluctuations in the human body. Thus, certain aged health measurements (e.g., questionnaire responses) are ignored or eliminated.

Illustrated processing block 212 determines if the questionnaire responses (e.g., answers to questions of the questionnaire) are expired. If not, illustrated processing block 214 returns a task with in-progress status meaning that the questions associated with the questionnaire responses do not need to be transmitted or answered by the patient. Rather, the questionnaire responses are relied on as the final answers to the questions. If the questionnaire responses are expired, illustrated processing block 216 returns a task with cancelled status meaning the questions associated with the questionnaire responses are to be transmitted to the patient for answering.

If processing block 204 determines that the questionnaire responses are not associated with the questionnaire, illustrated processing block 208 obtains the first questionnaire form. Illustrated processing block 210 returns a task with a non-started status meaning that the questions of the questionnaire can be transmitted to the patient and dependent on the various other checks (e.g., adaptive flows) described herein.

Figure 4:
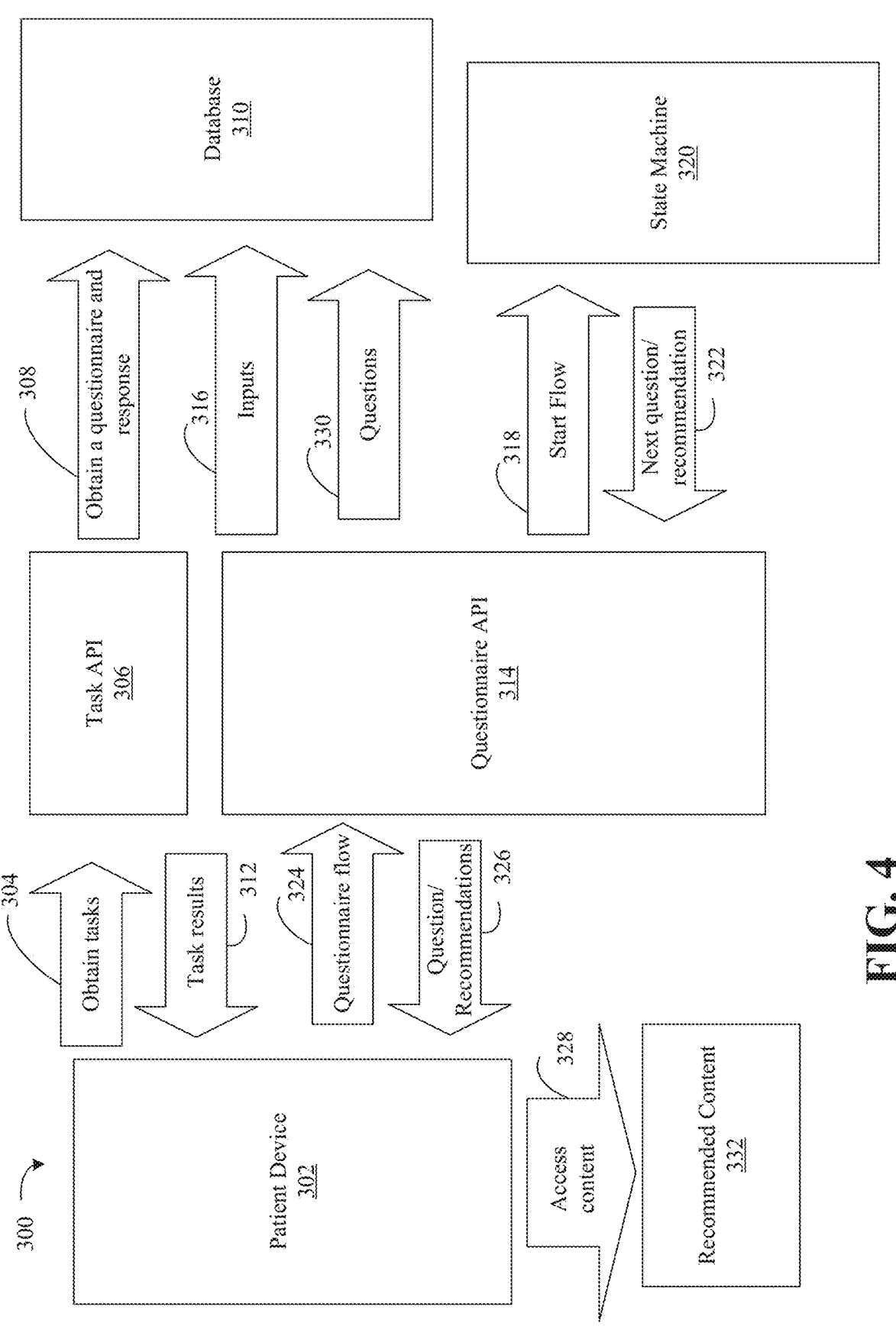
FIG. 4 is a diagram of an example of a questionnaire and recommendation process according to an embodiment.

FIG. 4 illustrates a questionnaire and recommendation process 300. The questionnaire and recommendation process 300 can generally be implemented in conjunction with any of the embodiments described herein, for example the questionnaire generation, analysis and treatment process 100 (FIG. 1), questionnaire and recommendation architecture 192 (FIG. 2) and/or method 200 (FIG. 3).

A patient device 302 obtains tasks 304 from a task API 306. The task API 306 obtains a questionnaire and response 308 from a database 310. The task API 306 then provides the task results 312 to the patient device 302. The patient device 302 generates a questionnaire flow 324 to a questionnaire API 314. The questionnaire API 314 provides inputs 316 to the database 310. The questionnaire API 314 then starts a flow 318 with state machine 320. The state machine 320 (e.g., a rule adaptive flow controller) generates next questions and recommendations 322 for a patient. The questionnaire API 314 can translate the question/recommendation into a form that the patient device 302 can utilize and/or database 310 can utilize. The questionnaire API 314 provides the questions to the database 310, 330, and provides the translated question/recommendation 326 to the patient device 302. The patient device 302 can access the content 328 of the recommendation to provide the recommended content 332.

Figure 5:
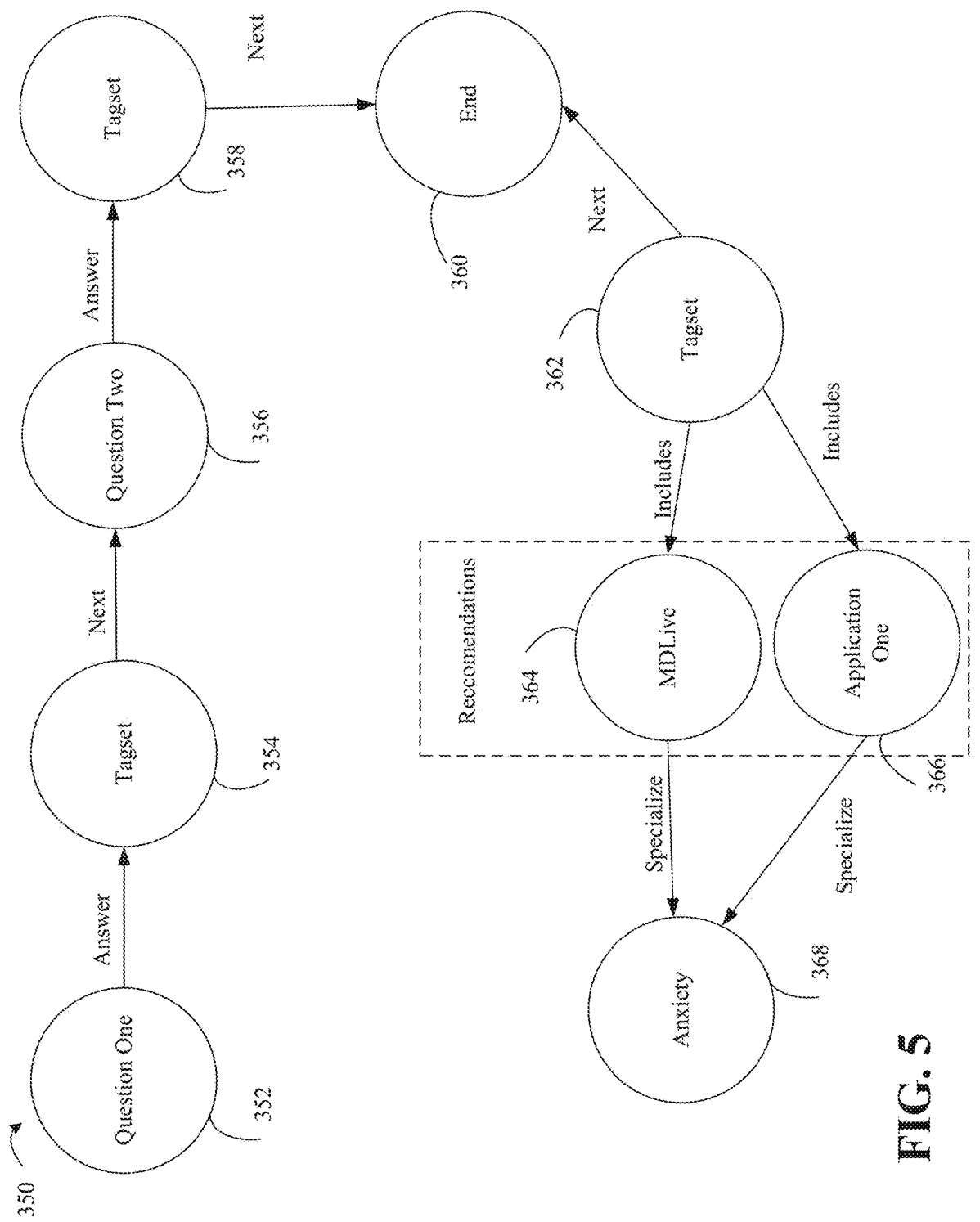
FIG. 5 is a diagram of an example of a directed-acyclic graph according to an embodiment.

FIG. 5 illustrates a directed-acyclic graph 350 (can be stored in a graph database) which is a control flow of the adaptive flow controller, such as the graph adaptive flow controller 124 (FIG. 1). The directed-acyclic graph 350 can generally be implemented in conjunction with any of the embodiments described herein, for example the questionnaire generation, analysis and treatment process 100 (FIG. 1), questionnaire and recommendation architecture 192 (FIG. 2), method 200 (FIG. 3) and/or questionnaire and recommendation process 300 (FIG. 4). The nodes are composed of questions, recommendations, conditions/topics and a TagSet for grouping. Answers are modeled as edges in the directed-acyclic graph 350.

In this example, there are two questions, namely question one 352 and question two 356. A patient provides answers to both question one 352 and question two 356. Embodiments can then execute a search based on the answers to determine that the patient has anxiety 368. Thus, the graph 350 is generated to treat the anxiety with recommendations including a live doctor visit shown as MDlive 364, and application one 366 (e.g., calming application). Thus, particular recommendations are geared towards a specific topic (anxiety) in the directed-acyclic graph 350. The recommendations are presented to the patient.

The tagsets 354, 358, 362 are pre-processing and/or post processing nodes that are used to interconnect the node of question one 352 and the node of question two 356 to other nodes and retrieve data required by operations (e.g., represent queries into a graph database to retrieve information). Furthermore, the tagset 362 node can connect to an end node 360 to determine when the flow ends, and to also connect to the recommendations.

Figure 6:
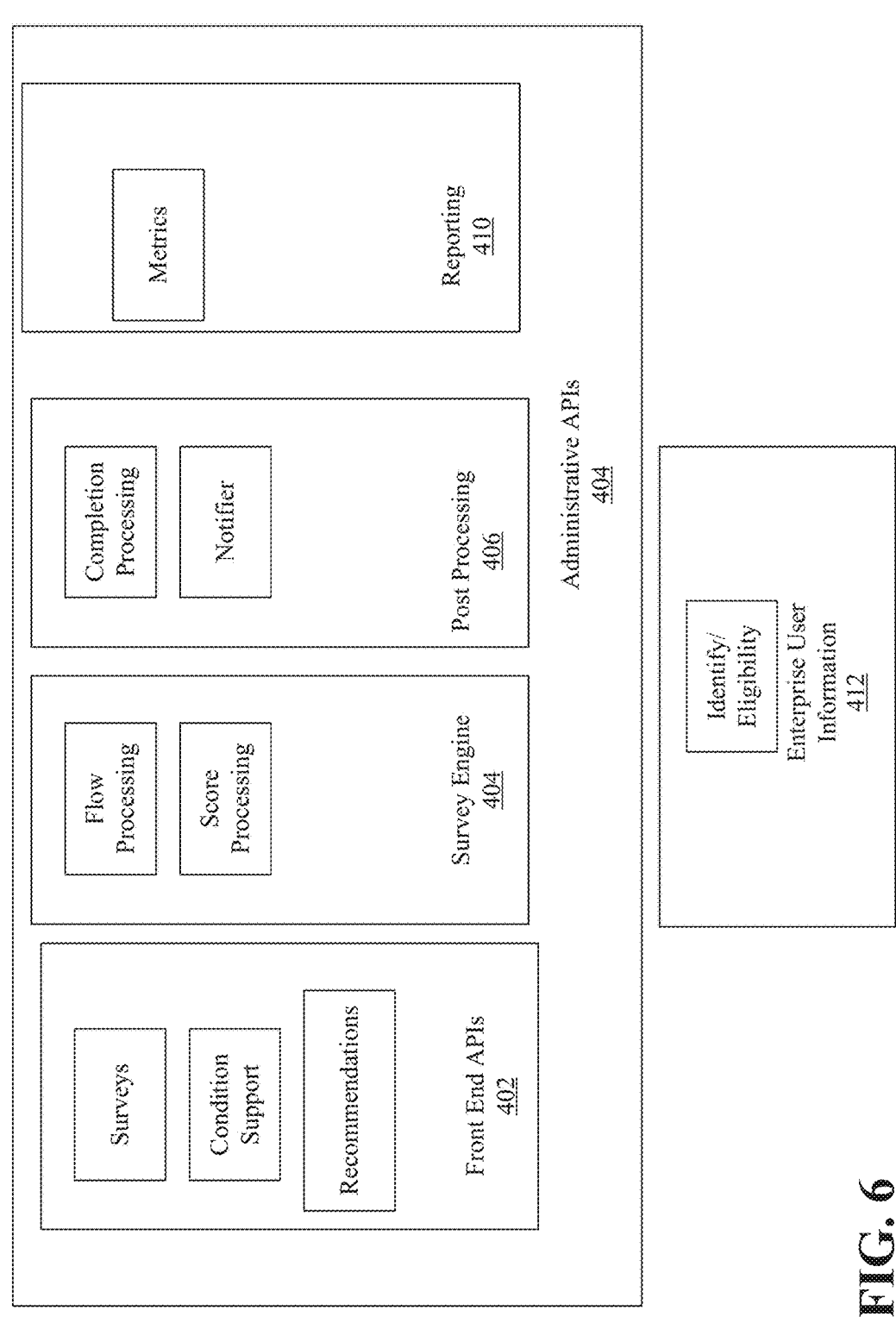
FIG. 6 is a block diagram of an example of an application programming interface architecture 400 according to an embodiment.

FIG. 6 illustrates an API architecture 400 that can implement aspects as described herein. The API architecture 400 can generally be implemented in conjunction with any of the embodiments described herein, for example the questionnaire generation, analysis and treatment process 100 (FIG. 1), questionnaire and recommendation architecture 192

(FIG. 2), method 200 (FIG. 3), questionnaire and recommendation process 300 (FIG. 4) and/or directed-acyclic graph 350 (FIG. 5). As illustrated the API architecture 400 can include front end APIs 402 including surveys (e.g., questionnaires) used to retrieve surveys, send survey response and determine statuses of on-going surveys. A condition support API provides information around topics based on a survey response from a patient. Recommendations API is included to handle situation if the survey provides a recommendation for example a third party product, coaching capability etc. The recommendations API returns such recommendations.

A survey engine 404 includes a flow processing API which determines, based on rules, a survey flow. The flow processing API is also responsible for determining if a score or recommendation is necessary. The score processing API calculates a score for recommendations and patient replies. Each questionnaire is assigned the score processing API making the system unaware of detail implementations of the scoring processing.

The post processing 406 can include completion processing and notifier APIs. The completion processing API is responsible for identifying which subsystem will process the survey result. The notifier API notifies downstream components of the result of the survey. A reporting API 410 can gather user interaction with the system, scoring history, possible conditions reference from external systems to generate a final score. An enterprise user information 412 refers to a system that is located physically on a company enterprise system as opposed to remotely located on a Cloud.

Figure 7A:
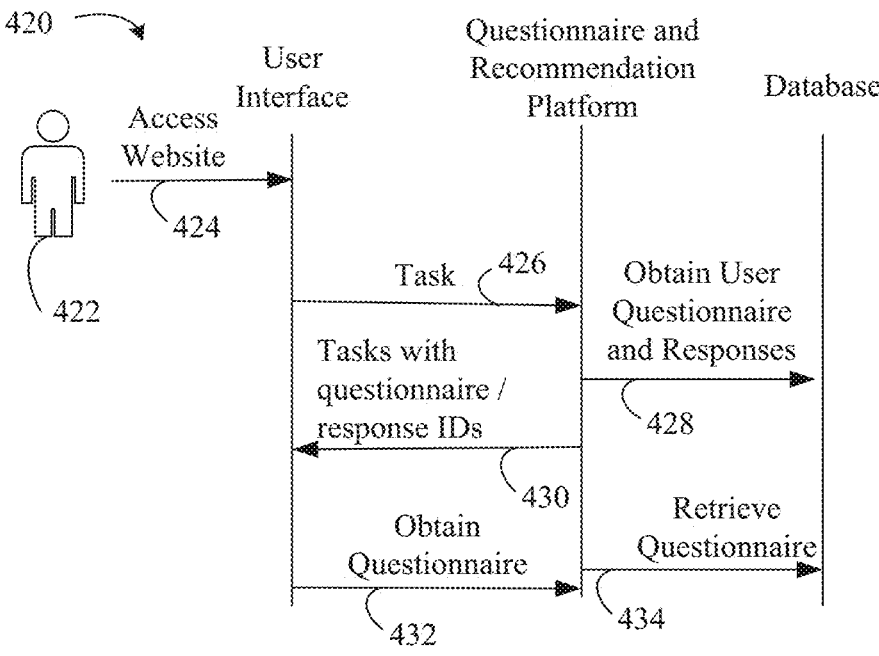
FIG. 7A is a diagram of an example of a questionnaire rendering process according to an embodiment.

FIG. 7A illustrates a questionnaire rendering process 420. The questionnaire rendering process 420 can generally be implemented in conjunction with any of the embodiments described herein, for example the questionnaire generation, analysis and treatment process 100 (FIG. 1), questionnaire and recommendation architecture 192 (FIG. 2), method 200 (FIG. 3), questionnaire and recommendation process 300 (FIG. 4), directed-acyclic graph 350 (FIG. 5) and/or API architecture 400 (FIG. 6). A patient 422 accesses a website 424 through a user interface.

A task 426 endpoint is invoked by a user interface to cause the questionnaire and recommendation platform to provide a set of tasks (that includes the questionnaire) back to the user interface (explained below in further detail). The questionnaire and recommendation platform obtains user questionnaire and responses 428. The questionnaire and recommendation platform then provides the tasks with questionnaire/response IDs 430 to the user interface, and thus returns the questionnaire identifier and questionnaire response identifier (for in-progress questionnaires). That is, the questionnaire and recommendation platform provides a set of tasks (that includes the questionnaire) back to the user interface for execution. The user interface then obtains the questionnaire 432 from the questionnaire and recommendation platform. The questionnaire and recommendation platform in turn retrieves further questions of the questionnaire 434 from the database. The questionnaire can be displayed by the user interface.

Figure 7B:
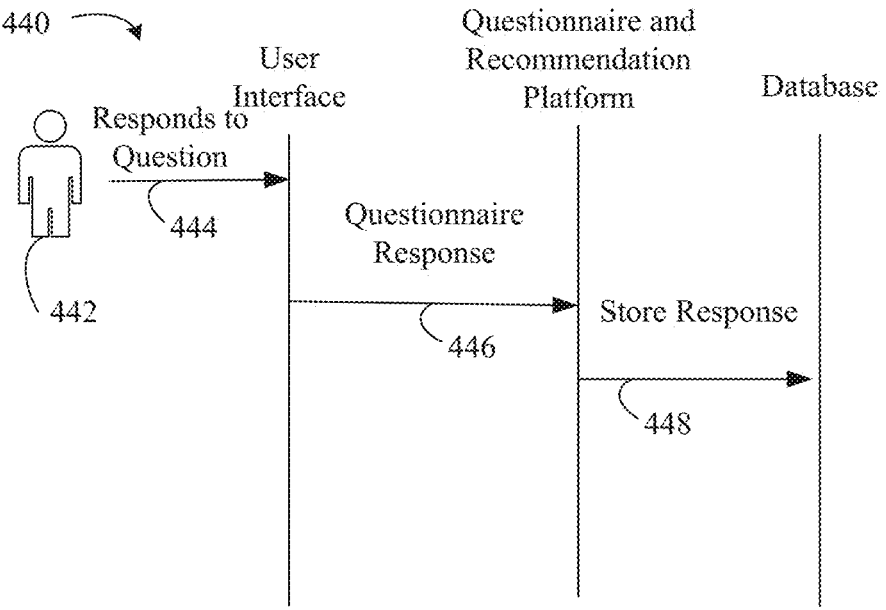
FIG. 7B is a diagram of an example of a reply process according to an embodiment.

FIG. 7B illustrates a reply process 440. The reply process 440 can generally be implemented in conjunction with any of the embodiments described herein, for example the questionnaire generation, analysis and treatment process 100 (FIG. 1), questionnaire and recommendation architecture 192 (FIG. 2), method 200 (FIG. 3), questionnaire and recommendation process 300 (FIG. 4), directed-acyclic graph 350 (FIG. 5), API architecture 400 (FIG. 6) and/or questionnaire rendering process 420 (FIG. 7A). A patient 442 responds to a question 444. The questionnaire and recommendation platform (or underlying hardware model) in turn processes the questionnaire response 446. The questionnaire and recommendation platform then stores the response 448 in the database.

Figure 8:
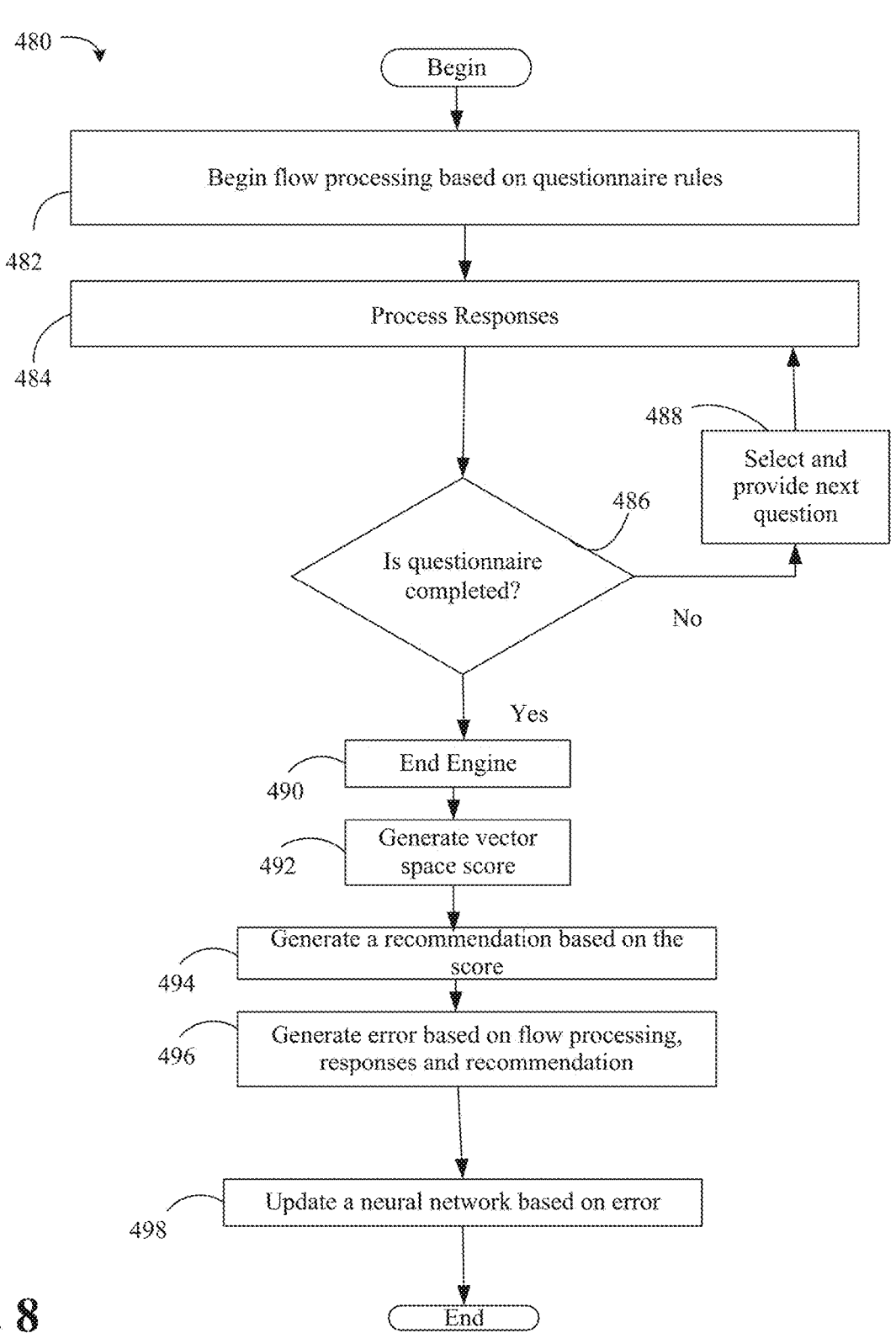
FIG. 8 is a flowchart of an example of a method of determining recommendations, providing recommendations and updating a neural network according to an embodiment.

FIG. 8 illustrates a method 480 of determining if questions of a questionnaire are to be asked based on patient data, providing recommendations and training a neural network. The method 480 can generally be implemented in conjunction with any of the embodiments described herein, for example the questionnaire generation, analysis and treatment process 100 (FIG. 1), questionnaire and recommendation architecture 192 (FIG. 2), method 200 (FIG. 3), questionnaire and recommendation process 300 (FIG. 4), directed-acyclic graph 350 (FIG. 5), API architecture 400 (FIG. 6), questionnaire rendering process 420 (FIG. 7A) and/or reply process 440 (FIG. 7B). In an embodiment, the method 480 is implemented in logic instructions (e.g., software), configurable logic, fixed-functionality hardware logic, computer readable instructions stored on at least one non-transitory computer readable storage medium that are executable to implement method 480, circuitry, etc., or any combination thereof.

Illustrated processing block 482 begins flow processing based on questionnaire rules. Illustrated processing block 484 processes responses. Illustrated processing block 486 determines if the questionnaire is completed. If not, illustrated processing block 488 selects and provides a next question. If the survey is completed, illustrated processing block 490 ends an engine (e.g., a questionnaire engine such as an adaptive or non-adaptive flow controller). Illustrated processing block 492 generates a vector space score (e.g., between recommendation vectors and a patient vector). A neural network can generate the vector space score. Illustrated processing block 494 generates a recommendation based on the score. Illustrated processing block 496 generates an error (e.g., with a neural network) based on flow processing, responses and recommendation. Illustrated processing block 498 updates a neural network based on the error.

Figure 9:
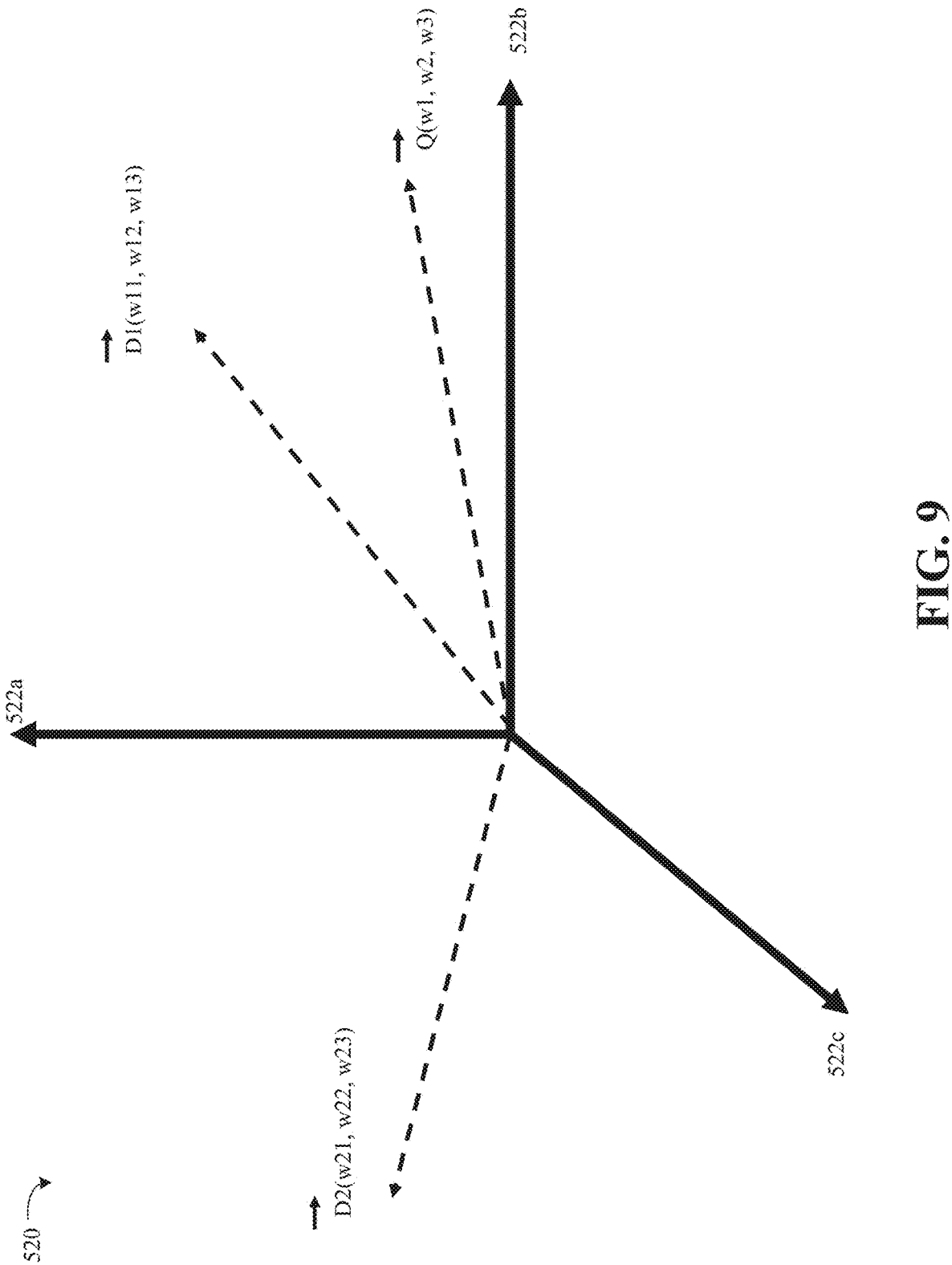
FIG. 9 is a diagram of an example of a vector space according to an embodiment.

FIG. 9 illustrates a vector space 520 to execute content based filtering with a QRC. In the vector space 520, w corresponds to weights (e.g., defines orientation/space), Q corresponds to queries and D corresponds to documents. The vector space 520 can be generated by a machine learning architecture, such as the MLQRM 116 (FIG. 1), to determine recommendation vectors that are closest to a patient vector (query vector). Thus, the vector space 520 can be a part of the embodiments described herein, such as questionnaire and recommendation process 300 (FIG. 4), directed-acyclic graph 350 (FIG. 5), and/or method 480 (FIG. 8).

In this example, several vectors are illustrated and mapped along several axes 522a-522c. Vector D1 corresponds to a first recommendation vector (e.g., a first recommendation), vector D2 corresponds to a second recommendation vector (e.g., a second recommendation) and vector Q corresponds to a query vector (e.g., a patient vector). A similarity score between the first vector D1 and the query vector Q is provided by Equation 2 below:

$$\text{Similarity } D1 \text{ and Query} = \text{sim}(D1, Q) = D1*q = w11*w1 + w12*w2 + w13*w3 \qquad \text{Equation 2}$$

Similarly, a similarity score between second vector D2 and query vector Q can be calculated. Embodiments select one of the first vector D1 and the second vector D2 based on the similarity scores. That is, one vector of the first vector D1 and the second vector D2 that is most similar to the query vector Q as measured by the similarity scores is selected for a recommendation to a patient associated with the query vector Q. A recommendation associated with the one vector is identified and provided to the patient. It will be understood that more or less dimensions can be provided by adjusting the amount of axes.

Figure 10:
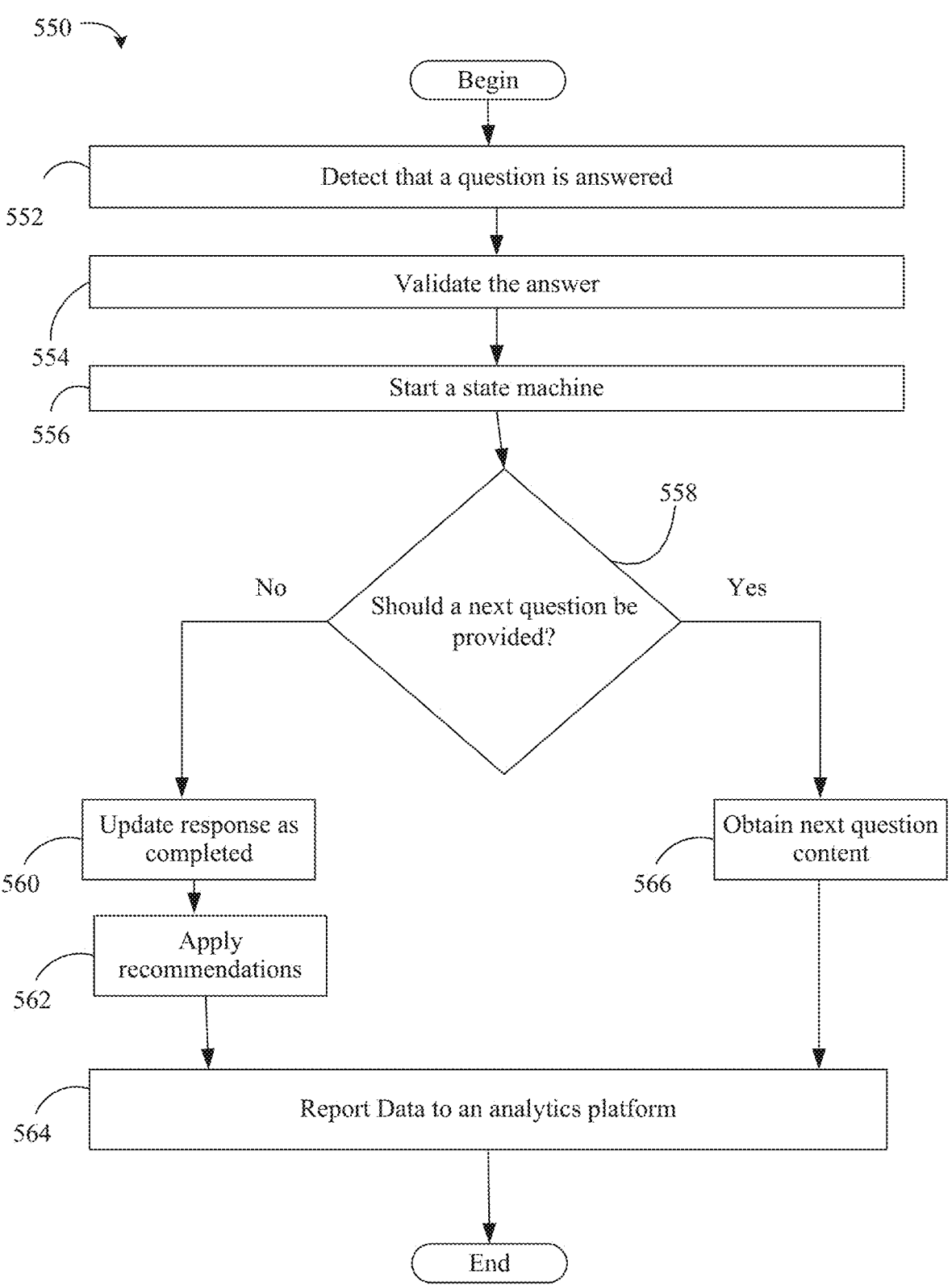
FIG. 10 is a flowchart of an example of generating questions with a rules based controller and updating a neural network according to an embodiment.

FIG. 10 illustrates a method 550 of generating questions with a rules based controller. The method 550 can generally be implemented in conjunction with any of the embodiments described herein, for example, the questionnaire generation, analysis and treatment process 100 (FIG. 1), questionnaire and recommendation architecture 192 (FIG. 2), method 200 (FIG. 3), questionnaire and recommendation process 300 (FIG. 4), directed-acyclic graph 350 (FIG. 5), API architecture 400 (FIG. 6), questionnaire rendering process 420 (FIG. 7A), reply process 440 (FIG. 7B), method 480 (FIG. 8) and/or vector space 520 (FIG. 9). In an embodiment, the method 550 is implemented in logic instructions (e.g., software), configurable logic, fixed-functionality hardware logic, computer readable instructions stored on at least one non-transitory computer readable storage medium that are executable to implement method 550, circuitry, etc., or any combination thereof.

Illustrated processing block 552 detects that a question is answered. Illustrated processing block 554 validates the answer. Illustrated processing block 556 starts a state machine. Illustrated processing block 558 determines if a next question should be provided. The state machine can execute processing block 558. If so, illustrated processing block 566 obtains the next question content. Processing block 566 can be executed with the state machine. If processing block 558 determines that the next question should not be provided, illustrated processing block 560 updates a response as completed (e.g., questionnaire completed). Illustrated processing block 562 applies recommendations. Illustrated processing block 564 reports data to an analytics platform.

Figure 11:
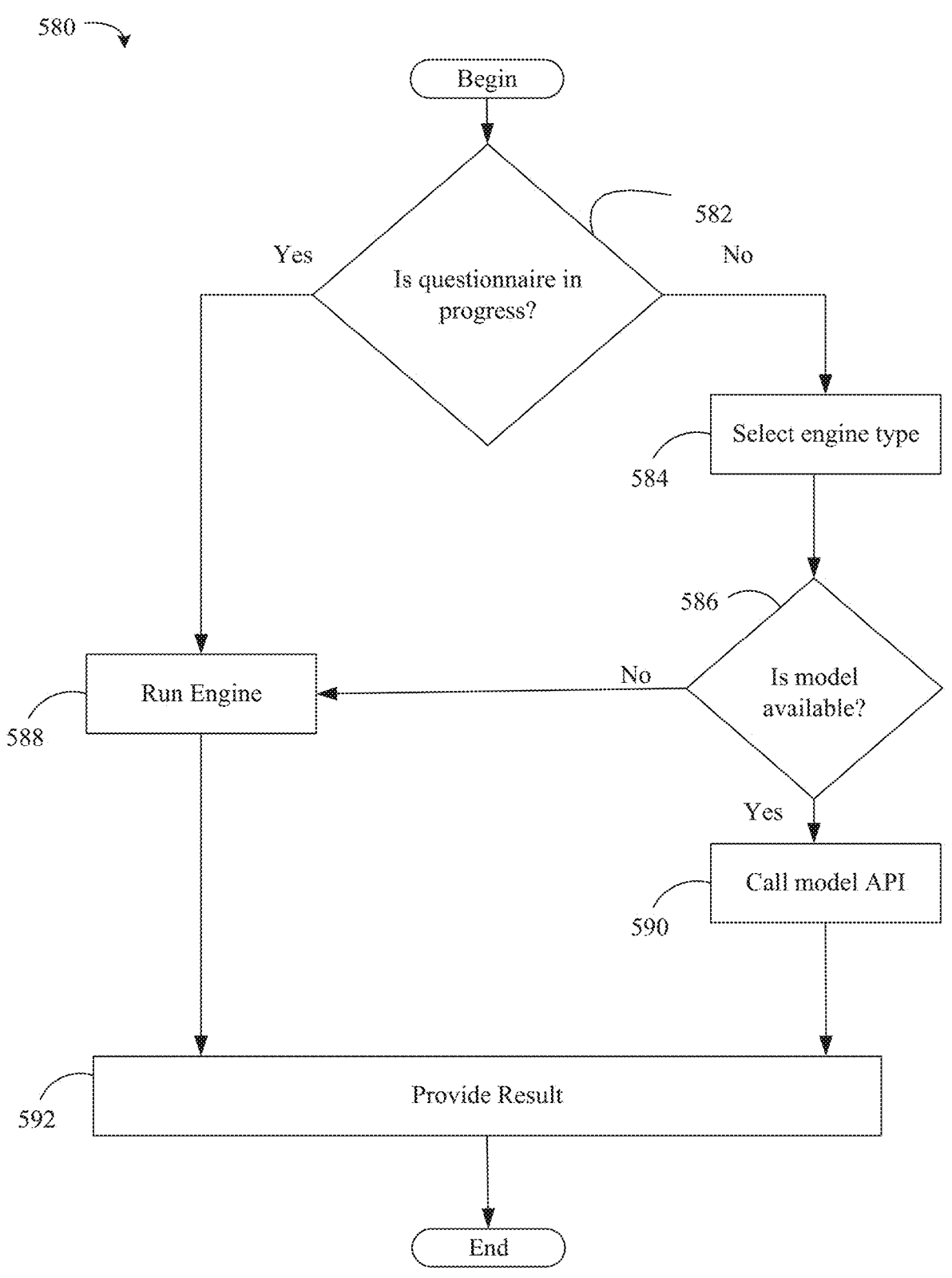
FIG. 11 is a flowchart of an example of selecting an engine for question flows according to an embodiment.

FIG. 11 illustrates a method 580 of selecting an engine (e.g., controller) for question flows. The method 580 can generally be implemented in conjunction with any of the embodiments described herein, for example, the questionnaire generation, analysis and treatment process 100 (FIG. 1), questionnaire and recommendation architecture 192 (FIG. 2), method 200 (FIG. 3), questionnaire and recommendation process 300 (FIG. 4), directed-acyclic graph 350 (FIG. 5), API architecture 400 (FIG. 6), questionnaire rendering process 420 (FIG. 7A), reply process 440 (FIG. 7B), method 480 (FIG. 8), vector space 520 (FIG. 9) and/or method 550 (FIG. 10). In an embodiment, the method 580 is implemented in logic instructions (e.g., software), configurable logic, fixed-functionality hardware logic, computer readable instructions stored on at least one non-transitory computer readable storage medium that are executable to implement method 580, circuitry, etc., or any combination thereof.

Illustrated processing block 582 determines if the questionnaire is in progress. If so, illustrated processing block 588 runs an engine (e.g., linear adaptive flow controller, a rule adaptive flow controller, a graph adaptive flow controller or non-adaptive flow controller). If illustrated processing block 582 determines that the questionnaire is not in progress, illustrated processing block 584 selects an engine type (e.g., linear adaptive flow controller, a rule adaptive flow controller, a graph adaptive flow controller or non-adaptive flow controller) to execute the questionnaire. Illustrated processing block 586 determines if a model (e.g., a machine learning question and recommendation model) is available to determine which questions to provide to the patient. If the model is not available, processing block 588 executes. Otherwise, illustrated processing block 590 calls the model API so that the model can operate with a patient device. Illustrated processing block 592 provides results.

Figure 12:
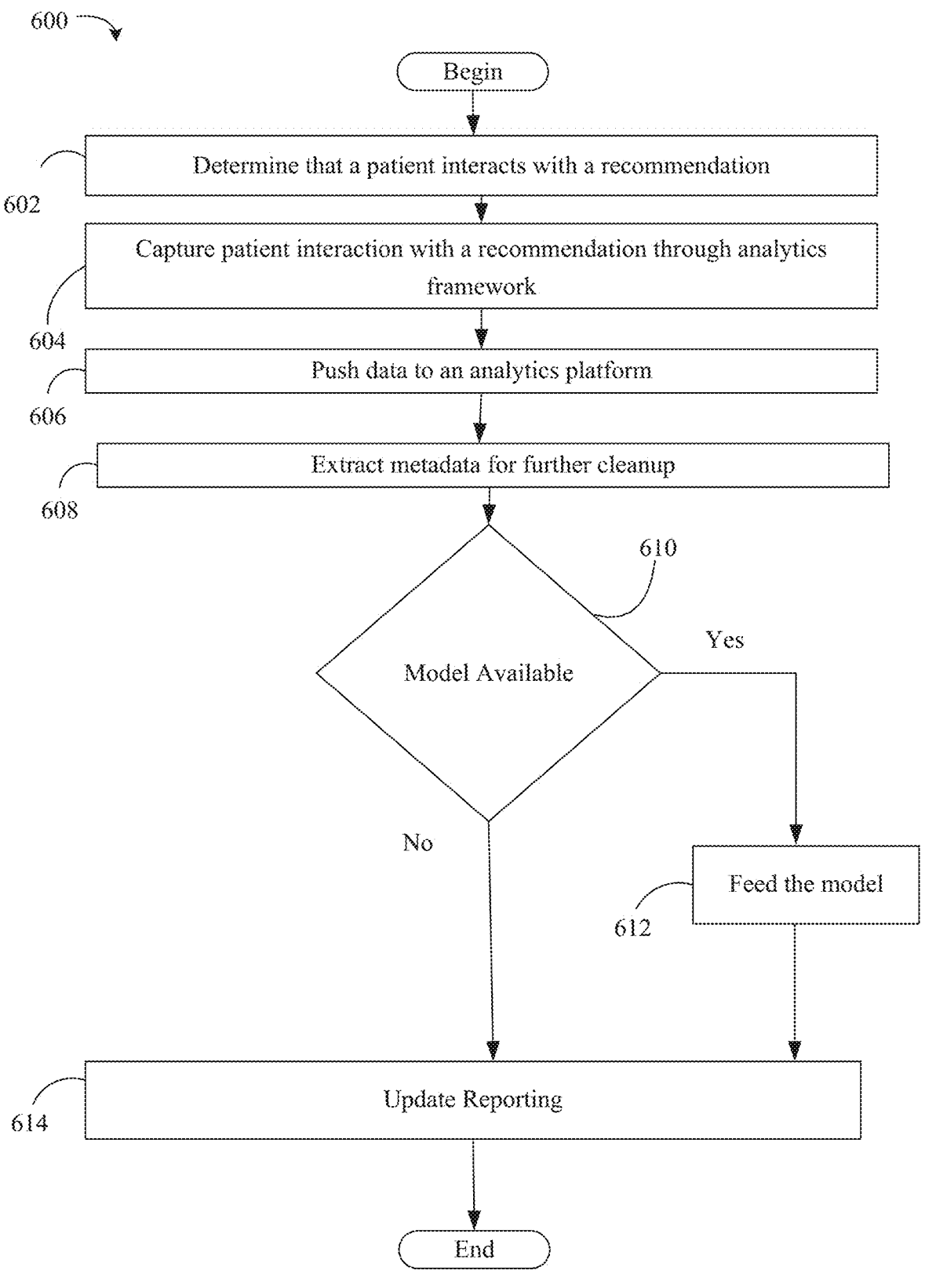
FIG. 12 is a flowchart of an example of capturing patient interactions and feeding a model based on the patient interactions according to an embodiment.

FIG. 12 illustrates a method 600 of capturing patient interactions and feeding a model based on the patient interactions. The method 600 can generally be implemented in conjunction with any of the embodiments described herein, for example the questionnaire generation, analysis and treatment process 100 (FIG. 1), questionnaire and recommendation architecture 192 (FIG. 2), method 200 (FIG. 3), questionnaire and recommendation process 300 (FIG. 4), directed-acyclic graph 350 (FIG. 5), API architecture 400 (FIG. 6), questionnaire rendering process 420 (FIG. 7A), reply process 440 (FIG. 7B), method 480 (FIG. 8), vector space 520 (FIG. 9), method 550 (FIG. 10) and/or method 580 (FIG. 11). In an embodiment, the method 600 is implemented in logic instructions (e.g., software), configurable logic, fixed-functionality hardware logic, computer readable instructions stored on at least one non-transitory computer readable storage medium that are executable to implement method 600, circuitry, etc., or any combination thereof.

Illustrated processing block 602 determines that a patient interacts with a recommendation. Illustrated processing block 604 captures a patient interaction with a recommendation through analytics framework. Illustrated processing block 606 pushes data to an analytics platform. Illustrated processing block 608 extracts metadata of the patient interactions for further cleanup. Illustrated processing block 610 determines if a model (e.g., a machine learning question and recommendation model) is available. If so, illustrated processing block 612 feeds (e.g., trains) the model with the patient interactions. Otherwise, illustrated processing block 614 updates the reporting.

Figure 13:
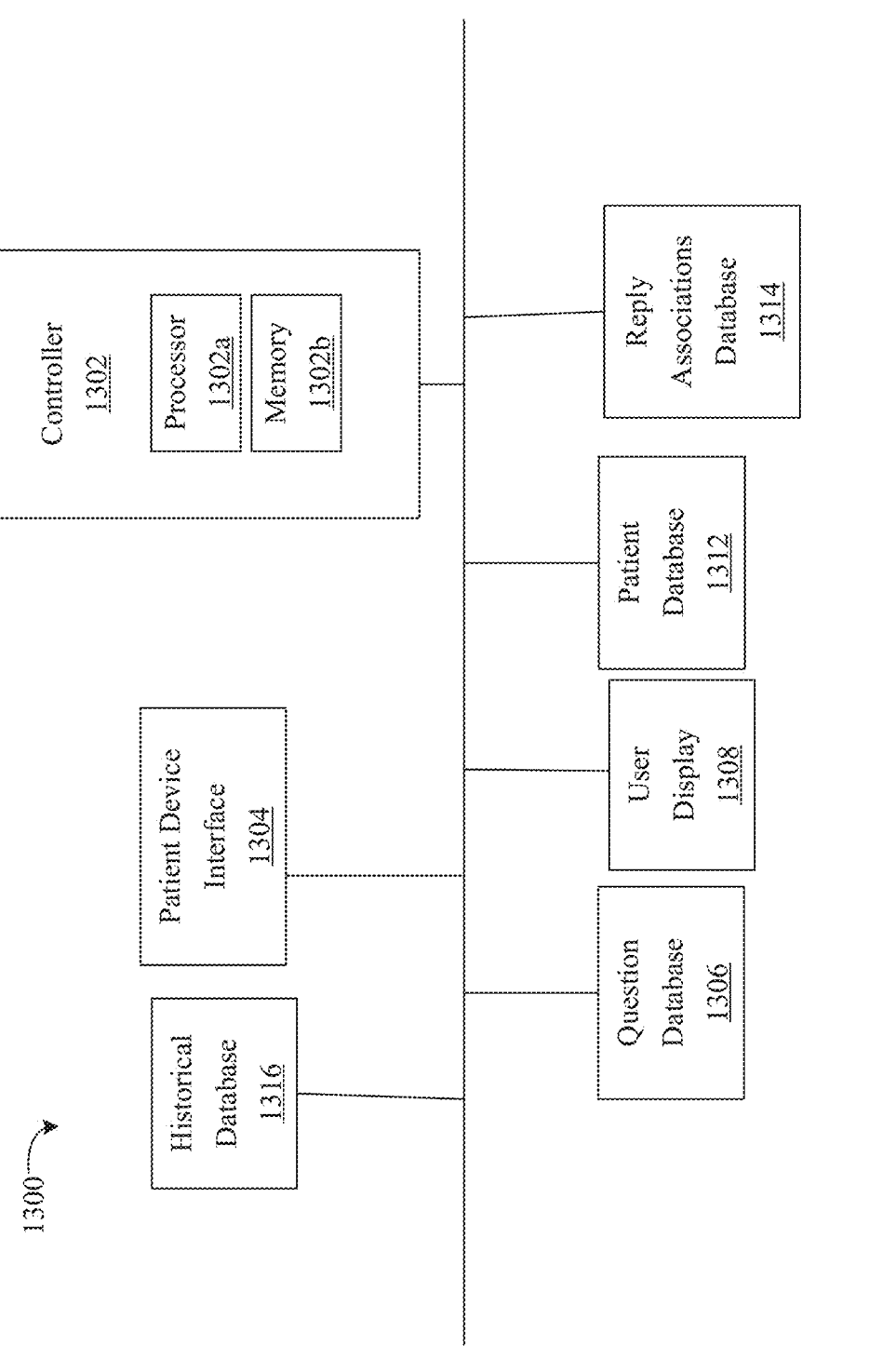
FIG. 13 is a block diagram of an example of a computing system according to an embodiment.

FIG. 13 shows a more detailed example of a computing system 1300 to generate questions for a questionnaire and generate recommendations. The illustrated computing system 1300 can be readily implement aspects related to, for example, the questionnaire generation, analysis and treatment process 100 (FIG. 1), questionnaire and recommendation architecture 192 (FIG. 2), method 200 (FIG. 3), questionnaire and recommendation process 300 (FIG. 4), directed-acyclic graph 350 (FIG. 5), API architecture 400 (FIG. 6), questionnaire rendering process 420 (FIG. 7A), reply process 440 (FIG. 7B), method 480 (FIG. 8), vector space 520 (FIG. 9), method 550 (FIG. 10), method 580 (FIG. 11) and/or method 600 (FIG. 12).

In the illustrated example, the computing system 1300 can include a patient device interface 1304 that can communicate with external devices (e.g., mobile devices, computers, smart watches, IoT devices, weigh scales, blood pressure cuff, etc.) to receive and provide patient recommendation, transmit questions to a patient device and receive replies to the questions. The computing system 1300 also includes a user display 1308 (e.g., audio and/or visual interface) to display recommendations, questions and/or replies and receive instructions from a user (e.g., an operator). A historical database 1316 stores patient interactions with recommendations, patient replies to questions and the questions. A patient database 1312 stores information specific to a patient that is to receive a questionnaire, such as EMRs, family history information, previous health measurements, etc.

A controller 1302 includes a processor 1302a (e.g., embedded controller, central processing unit/CPU) and a memory 1302*b* (e.g., non-volatile memory/NVM and/or volatile memory) containing a set of instructions, which when executed by the processor 1302*a*, cause the controller 1302 to implement any of the aspects described herein. For example, the controller 1302 can receive a patient request for a questionnaire from a patient device via the patient device interface 1304, where the questionnaire is associated with a plurality of questions stored in the question database 1306. The controller 1302 can further access the question database 1306 to select a first question from the plurality of questions, cause the first question to be transmitted to the patient device via the patient device interface 1304 and identify a first patient reply from the patient device, where the first patient reply is a reply to the first question. The controller 1302 can further access the question database 1306 to select a second question from the plurality of questions based on the first patient reply. The controller 1302 can further cause the second question to be transmitted to the patient device via the patient device interface 1304, receive a second patient reply in response to the second question from the patient device via the patient device interface 1304, determine, with a machine learning recommendation model, a patient recommendation based on the first and second patient replies, and cause the patient recommendation to be transmitted to the patient device via the patient device interface 1304. In some examples, the first and second replies to the first and second questions can be stored in association with the first and second questions in the reply association database 1314. In some examples, the patient database 1312 can be accessed to retrieve data associated with the patient to identify appropriate questions for the patient and generate recommendations.

Figure 14:
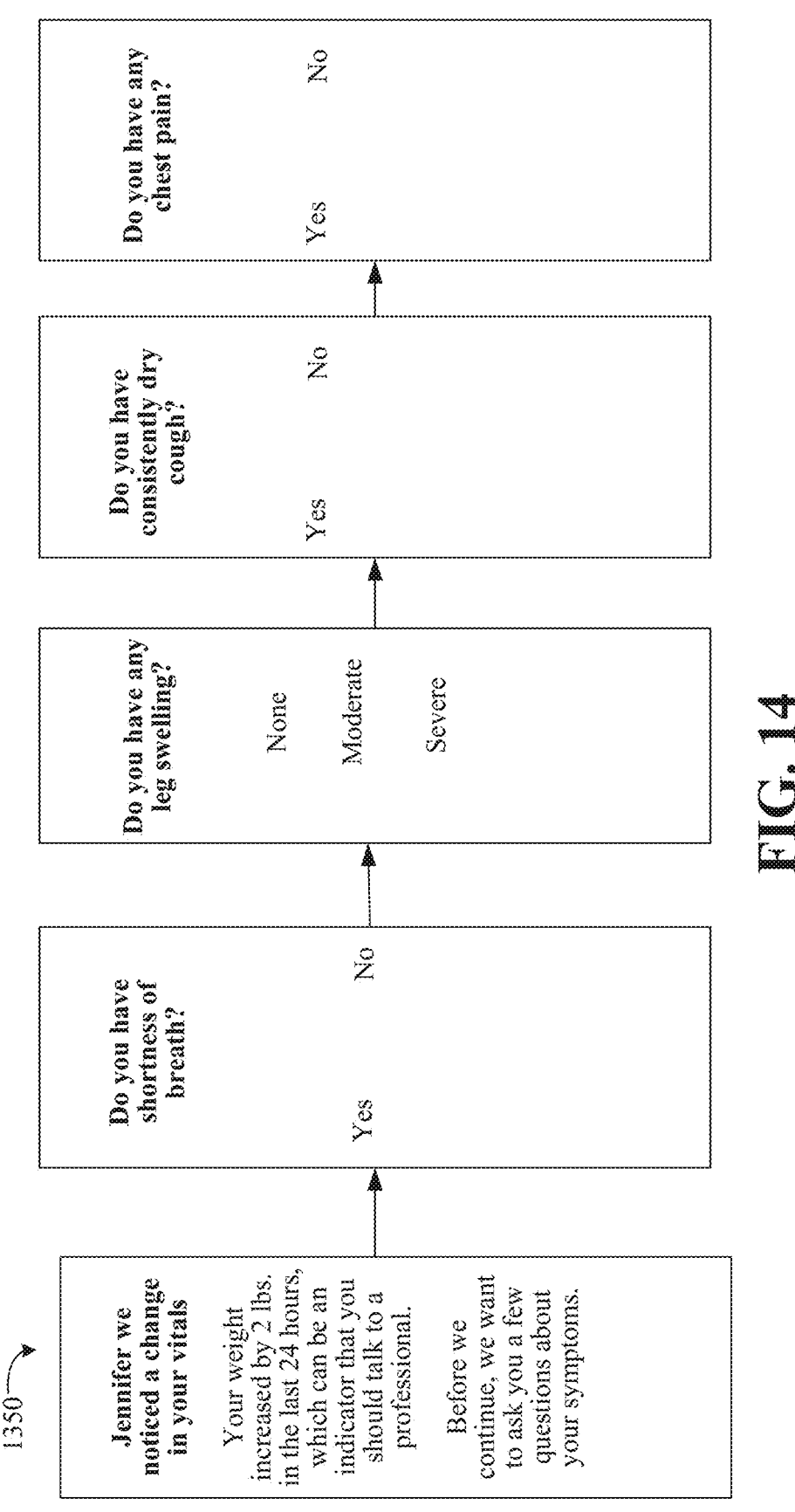
FIG. 14 is a diagram of an example of a graphical user interface that illustrates a series of questions according to an embodiment.

FIG. 14 illustrates a graphical user interface 1350 that illustrates a series of questions. The graphical user interface 1350 can generally be implemented in conjunction with any of the embodiments described herein, for example the questionnaire generation, analysis and treatment process 100 (FIG. 1), questionnaire and recommendation architecture 192 (FIG. 2), method 200 (FIG. 3), questionnaire and recommendation process 300 (FIG. 4), directed-acyclic graph 350 (FIG. 5), API architecture 400 (FIG. 6), questionnaire rendering process 420 (FIG. 7A), reply process 440 (FIG. 7B), method 480 (FIG. 8), vector space 520 (FIG. 9), method 550 (FIG. 10), method 580 (FIG. 11), method 600 (FIG. 12) and/or computing system 1300 (FIG. 13). The graphical user interface 1350 can be displayed on a patient device. The questions are associated with a questionnaire generation process as described herein. A patient can reply to each of the questions by selecting one of the presented options (e.g., yes, no, none, moderate, severe) and provide the reply to a QRP platform as described herein. While not illustrated, another graphical user interface can show recommendations based on the replies.

Figure 15:
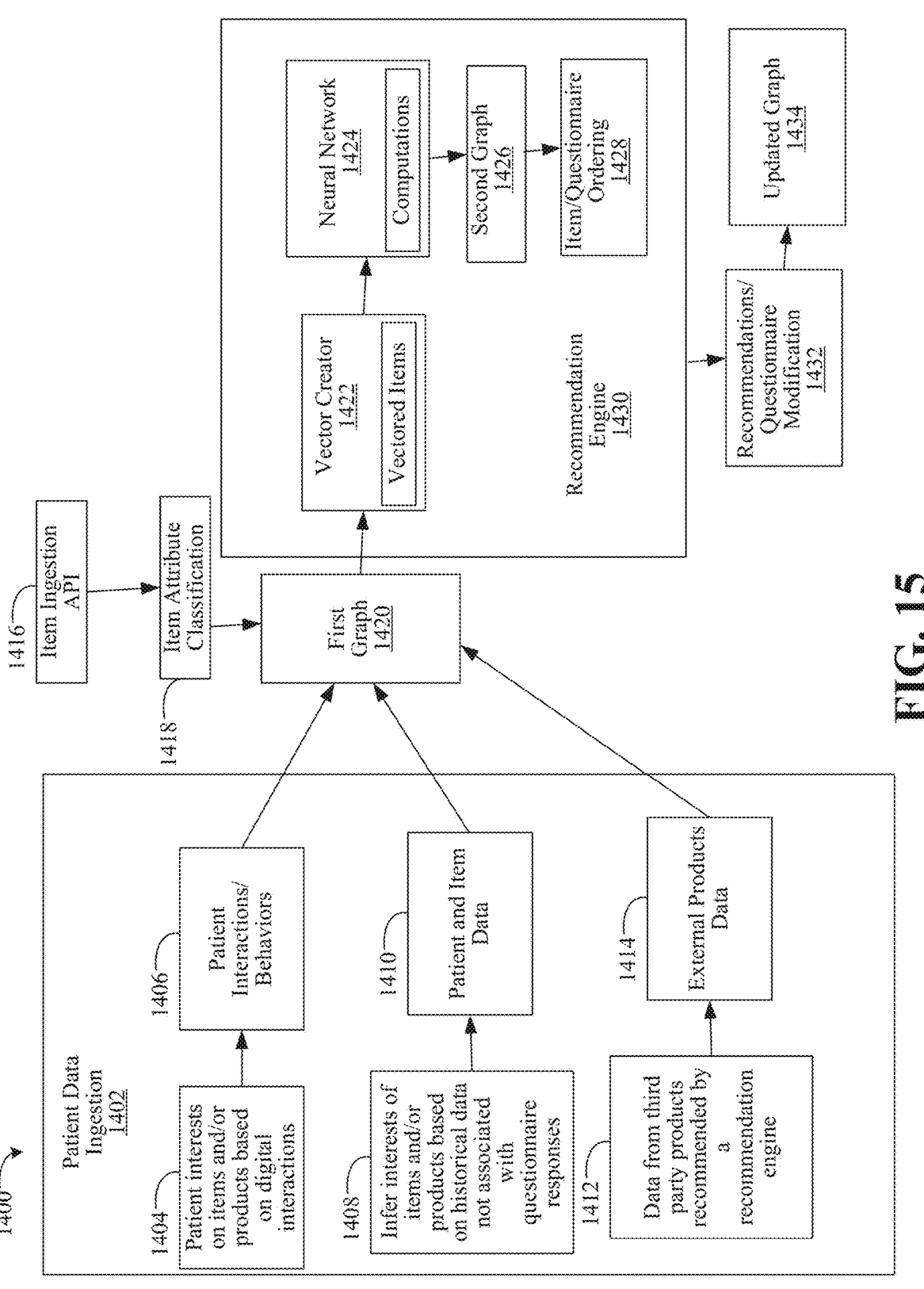
FIG. 15 is a diagram of an example of a process flow of patient interaction with a questionnaire and recommendation architecture according to an embodiment.

FIG. 15 illustrates a process flow 1400 of a patient interaction with a questionnaire and recommendation architecture according to some examples. The process flow 1400 can generally be implemented in conjunction with any of the embodiments described herein, for example the questionnaire generation, analysis and treatment process 100 (FIG. 1), questionnaire and recommendation architecture 192 (FIG. 2), method 200 (FIG. 3), questionnaire and recommendation process 300 (FIG. 4), directed-acyclic graph 350 (FIG. 5), API architecture 400 (FIG. 6), questionnaire rendering process 420 (FIG. 7A), reply process 440 (FIG. 7B), method 480 (FIG. 8), vector space 520 (FIG. 9), method 550

(FIG. 10), method 580 (FIG. 11), method 600 (FIG. 12), computing system 1300 (FIG. 13) and/or graphical user interface 1350 (FIG. 14).

Patient data ingestion 1402 includes retrieving data related to a patient. For example, the patient data ingestion 1402 identifies patient interests on items and/or products based on digital interactions 1404. The patient data ingestions 1402 can detect patient interactions/behaviors 1406 based on the patient interests on the items and/or products. The patient data ingestion 1402 infers interests of items and/or products based on historical data not associated with questionnaire responses 1408, and generates patient and item data 1410 based on the interests of the items and/or the products based on historical data not associated with questionnaire responses 1408. The patient data ingestion 1402 identifies data from third party products recommended by a recommendation engine 1412, and generates external products data 1414 based on the data from the third party products. The recommendation engine can be the recommendation engine 1430.

The process flow 1400 includes an item ingestion API 1416 that generates item attribute classification 1418. The process flow 1400 generates a first graph 1420 (e.g., representing different recommendations) based on the item attribute classification 1418, the patient interactions/behaviors 1406, the external products data 1414 and the patient and item data 1410. A vector creator 1422 generates vectored items. The neural network 1424 executes computations and generates a second graph 1426. The recommendation engine 1430 generates an item questionnaire ordering 1428. The process flow 1400 then generates recommendations/questionnaire modification 1432 to generate an updated graph 1434 which can be an updated version of the second graph 1426 or the first graph 1420.

Figure 16:
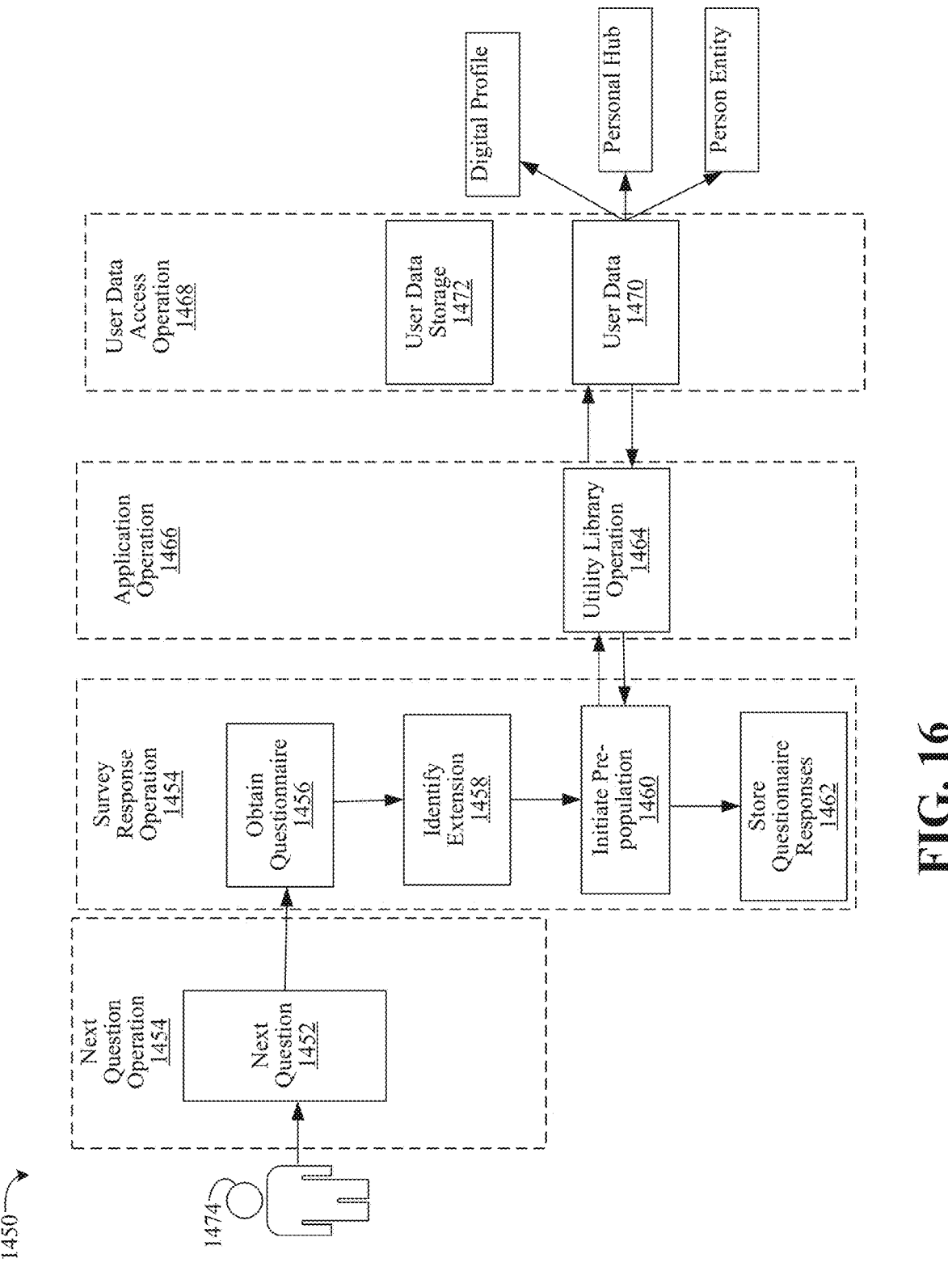
FIG. 16 is a diagram of an example of a process flow a questionnaire process according to an embodiment.

Turning now to FIG. 16, a detailed flow of a questionnaire process 1450 is illustrated. The questionnaire process 1450 can generally be implemented in conjunction with any of the embodiments described herein, for example the questionnaire generation, analysis and treatment process 100 (FIG. 1), questionnaire and recommendation architecture 192 (FIG. 2), method 200 (FIG. 3), questionnaire and recommendation process 300 (FIG. 4), directed-acyclic graph 350 (FIG. 5), API architecture 400 (FIG. 6), questionnaire rendering process 420 (FIG. 7A), reply process 440 (FIG. 7B), method 480 (FIG. 8), vector space 520 (FIG. 9), method 550 (FIG. 10), method 580 (FIG. 11), method 600 (FIG. 12), computing system 1300 (FIG. 13), graphical user interface 1350 (FIG. 14) and/or process flow 1400 (FIG. 15).

A user 1474 initiates (e.g., via a user request) the questionnaire. The process 1450 then executes a survey question operation 1454. At such a time, a user interface calls a function to obtain a next question 1452 to obtain questions to show on the user interface. A questionnaire definition can be extracted from a database. A questionnaire can also be obtained 1456. The questionnaire process 1450 then identifies extension 1458 to initiate pre-population 1460 of the questionnaire. The questionnaire process 1450 then utilizes utility library operation 1464 to generate user responses that can be stored as user data 1470. The utility library operation 1464 can call a user data library to obtain data from a source. The data can be returned to the utility library operation 1464 as "PatientData." The utility library operation 1464 converts the PatientData to an application resource (e.g., FHIR compliant resource). The utility library operation 1464 utilizes a path (e.g., FHIR compliant) to extract the values for a question. The utility library operation 1464 returns a questionnaire response and stores the questionnaire response 1462 on a database.

Figure 17:
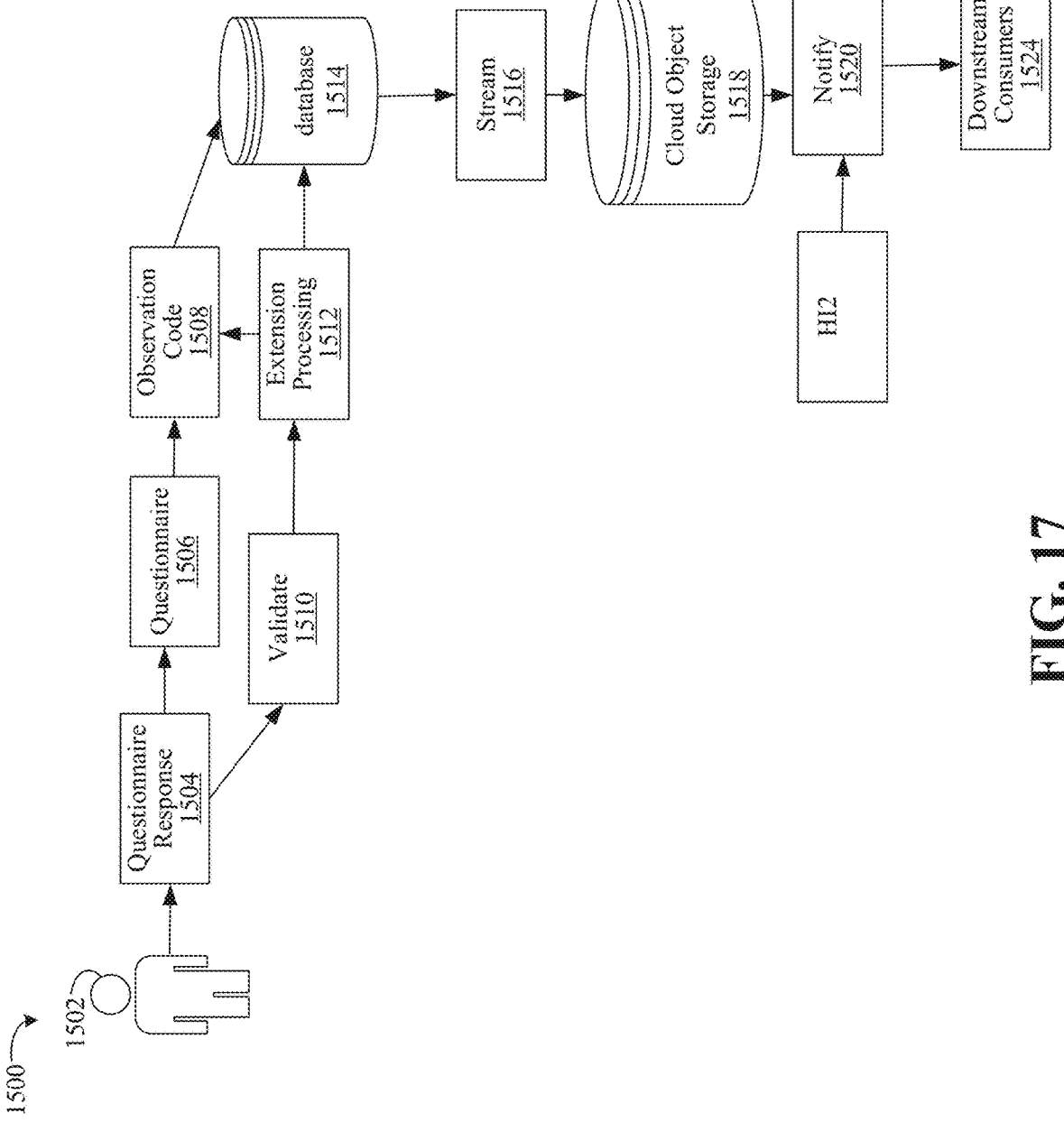
FIG. 17 is a detailed flow to extract an observation when a patient answers a question according to an embodiment.

Turning now to FIG. 17, a detailed flow 1500 to extract an observation when a patient answers a question. The detailed flow 1500 can generally be implemented in conjunction with any of the embodiments described herein, for example the questionnaire generation, analysis and treatment process 100 (FIG. 1), questionnaire and recommendation architecture 192 (FIG. 2), method 200 (FIG. 3), questionnaire and recommendation process 300 (FIG. 4), directed-acyclic graph 350 (FIG. 5), API architecture 400 (FIG. 6), questionnaire rendering process 420 (FIG. 7A), reply process 440 (FIG. 7B), method 480 (FIG. 8), vector space 520 (FIG. 9), method 550 (FIG. 10), method 580 (FIG. 11), method 600 (FIG. 12), computing system 1300 (FIG. 13), graphical user interface 1350 (FIG. 14), process flow 1400 (FIG. 15) and/or questionnaire process 1450 (FIG. 16).

Initially, a patient 1502 answers a question of a questionnaire 1506. The answer is the questionnaire response 1504. The questionnaire 1506 is retrieved. The questionnaire response 1504 is validated 1510. Extension processing is initiated to verify attached extensions in a questionnaire item of the questionnaire 1506 corresponding to the questionnaire response 1504. If the attached extensions are present, the questionnaire response can extract a value of answer as an observation object, referred to as observation code 1508. The observation code 1508 can be stored in the database 1514. A stream 1516 process is initiated. The data is stored on a cloud object storage 1518. A notification 1520 is sent to downstream consumers 1524.

Figure 18:
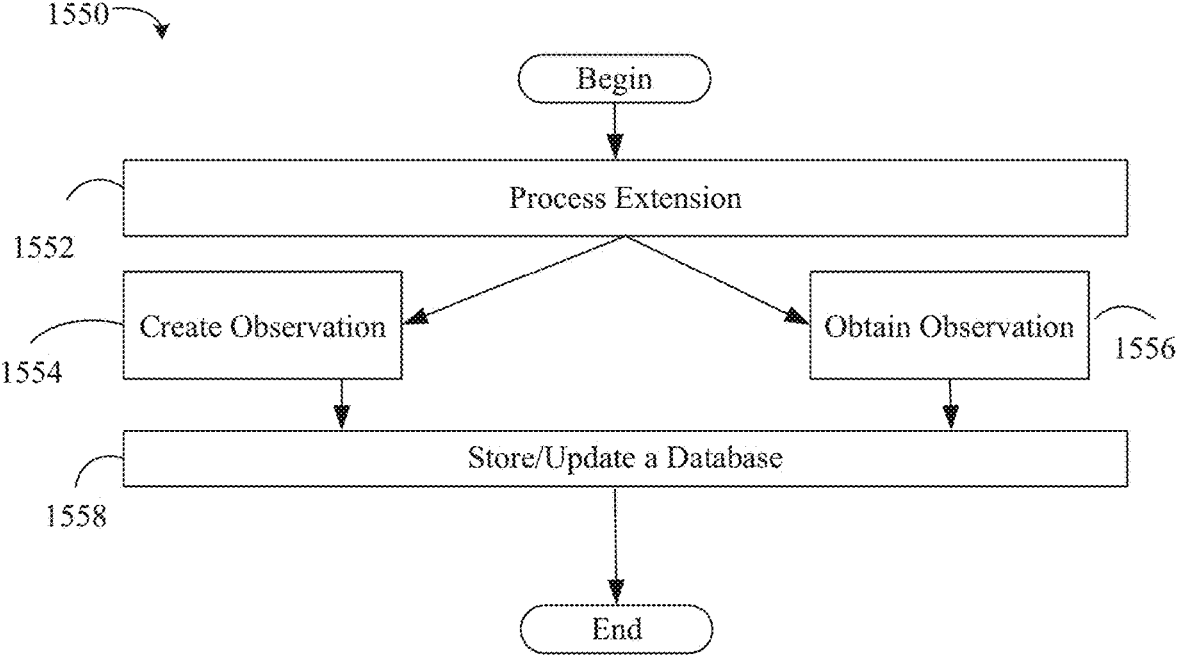
FIG. 18 is a state machine for a questionnaire observation-based extraction process according to an embodiment.

Turning now to FIG. 18, a state machine 1550 for a questionnaire observation-based extraction process is illustrated. The state machine 1550 can generally be implemented in conjunction with any of the embodiments described herein, for example the questionnaire generation, analysis and treatment process 100 (FIG. 1), questionnaire and recommendation architecture 192 (FIG. 2), method 200 (FIG. 3), questionnaire and recommendation process 300 (FIG. 4), directed-acyclic graph 350 (FIG. 5), API architecture 400 (FIG. 6), questionnaire rendering process 420 (FIG. 7A), reply process 440 (FIG. 7B), method 480 (FIG. 8), vector space 520 (FIG. 9), method 550 (FIG. 10), method 580 (FIG. 11), method 600 (FIG. 12), computing system 1300 (FIG. 13), graphical user interface 1350 (FIG. 14), process flow 1400 (FIG. 15), questionnaire process 1450 (FIG. 16) and/or a detailed flow 1500 (FIG. 17).

When a questionnaire response is received, examples identify that a question answer should be converted into an observation and the state machine 1550 (e.g., an asynchronous state machine) is initiated (e.g., a cloud based step function) to continue the observation process. One reason of using the state machine 1550 as an asynchronous state machine is to avoid blocking the questionnaire process (e.g., a user interface can continue to present questions and receive answers) while generating the observation. Thus, the observations can be generated in parallel with questions being generated and answers to the questions being obtained.

In this example, the state machine 1550 processes an extension 1552. The state machine then creates an observation 1554 and obtains an observation 1556. The state machine then stores/updates a database 1558.

Figures 19, 20:
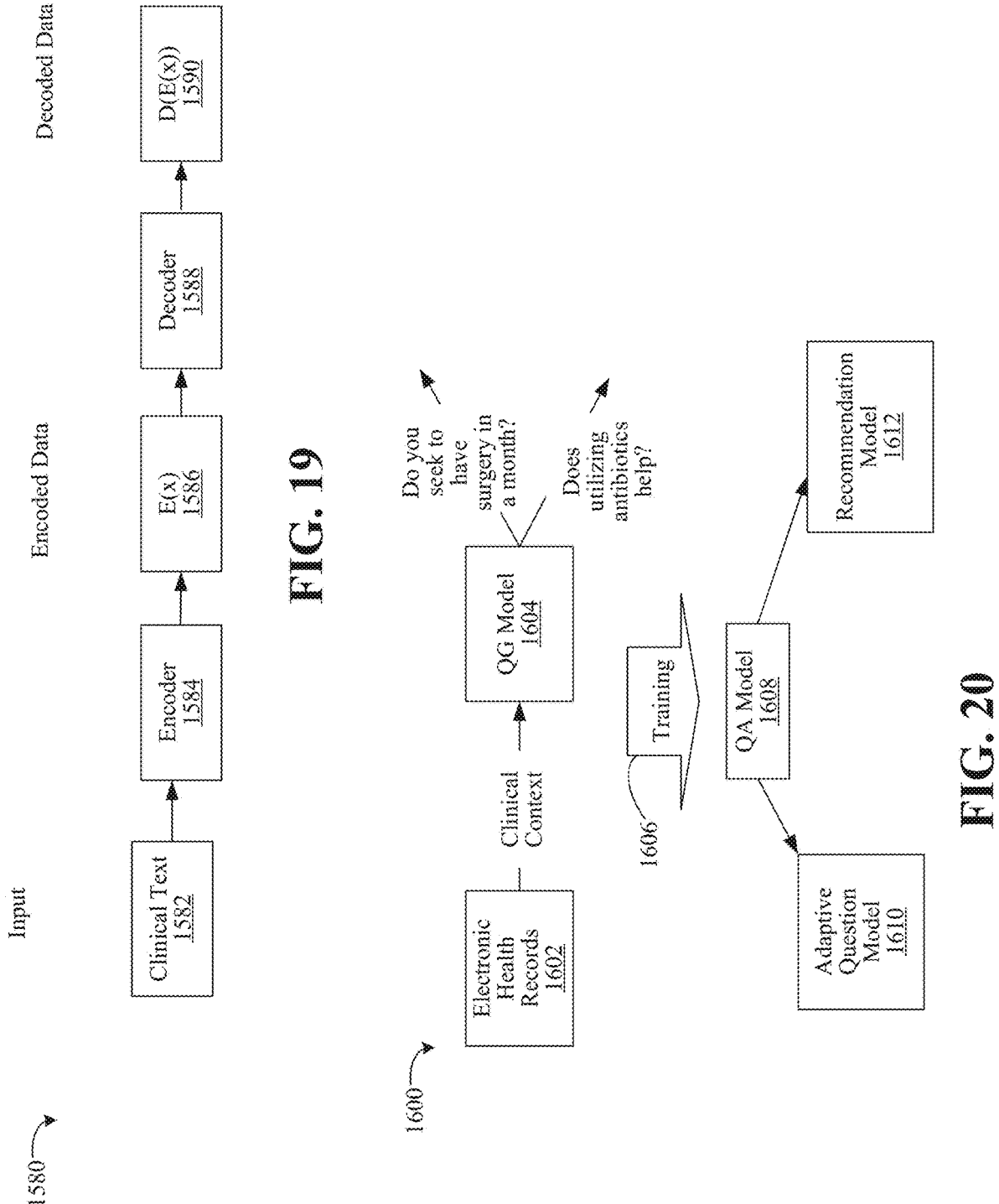
FIG. 19 is a generative model architecture according to an embodiment.
FIG. 20 is a model recommendation architecture according to an embodiment.

Turning now to FIG. 19, a generative model architecture 1580 is illustrated. The generative model architecture 1580 can generally be implemented in conjunction with any of the embodiments described herein, for example the questionnaire generation, analysis and treatment process 100 (FIG. 1), questionnaire and recommendation architecture 192 (FIG. 2), method 200 (FIG. 3), questionnaire and recommendation process 300 (FIG. 4), directed-acyclic graph 350 (FIG. 5), API architecture 400 (FIG. 6), questionnaire rendering process 420 (FIG. 7A), reply process 440 (FIG. 7B), method 480 (FIG. 8), vector space 520 (FIG. 9), method 550 (FIG. 10), method 580 (FIG. 11), method 600 (FIG. 12), computing system 1300 (FIG. 13), graphical user interface 1350 (FIG. 14), process flow 1400 (FIG. 15), questionnaire process 1450 (FIG. 16), a detailed flow 1500 (FIG. 17) and/or state machine 1550 (FIG. 18).

Examples can relate to questionnaires that are used for medical and/or clinical purposes. Such questionnaires are utilized to drive health product recommendations, generate care plans and/or activities and aid patients with useful medical information. The ability to generate medical questions is not a trivial task. In some cases, these questions are created by clinical experts and potentially rely on extensive historical knowledge of medical information.

The generative model architecture 1580 can be a question generator (QG) model (e.g., an artificial intelligence and/or machine learning model) that can utilize generative machine learning techniques to automatically create questions based on data from Electronic Medical Records (EMR) and clinical notes. Some examples utilize a generative model(s) to drive generation of dynamic questions and the recommendations. Such functions may operate with machine learning models to dynamically generate the best question to ask and later to recommend products to the user.

The generative model architecture 1580 (e.g., a QG model) is used to generate questions based on clinical text 1582. A source of the clinical text 1582 may originate from EHRs systems where clinical notes are generated and also utilize medical data sources. The QG Model utilizes an encoder 1584, function E(x) 1586, decoder 1588 and decoded data function D(E(x)) 1590 (e.g., a variational AutoEncoder (VAE) model) to generate new questions.

Turning now to FIG. 20, a model recommendation architecture 1600 is illustrated. The can generally be implemented in conjunction with any of the embodiments described herein, for example the questionnaire generation, analysis and treatment process 100 (FIG. 1), questionnaire and recommendation architecture 192 (FIG. 2), method 200 (FIG. 3), questionnaire and recommendation process 300 (FIG. 4), directed-acyclic graph 350 (FIG. 5), API architecture 400 (FIG. 6), questionnaire rendering process 420 (FIG. 7A), reply process 440 (FIG. 7B), method 480 (FIG. 8), vector space 520 (FIG. 9), method 550 (FIG. 10), method 580 (FIG. 11), method 600 (FIG. 12), computing system 1300 (FIG. 13), graphical user interface 1350 (FIG. 14), process flow 1400 (FIG. 15), questionnaire process 1450 (FIG. 16), a detailed flow 1500 (FIG. 17), state machine 1550 (FIG. 18) and/or generative model architecture 1580 (FIG. 19).

The overall architecture of the model recommendation architecture 1600 (e.g., a generative model) is illustrated. The following is utilized to generate new questions and also aid the recommendation model training of the model recommendation architecture 1600 to provide relevant and enhanced recommendations. Data is extracted from EHRs 1602 (e.g., clinical notes). The QG model 1604 utilizes the EHRs 1602 in order to generate new questions (e.g., "do you seek to have surgery in a month?" and "does utilizing antibiotics help?"). The questions generated by the QG model 1604 are then fed to a Question Answer (QA) Model 1608 to generate answers for the questions. The QG questions are then fed to the Adaptive Question Model 1610 and/or the recommendation model 1612 in order to increase training data to predict the next question to ask the user.

The present methods and systems for generating models for questions can further operate on historical patient records to determine if the correct questions are being asked to improve health outcomes. A type of patient records can be a longitudinal patient record (LPR), which can include a comprehensive medical profile of the patient sourced from numerous care providers, pharmacies, hospitals, third-party medical data vendors, the patient data, and the claims data, etc. The LPR can be a machine readable file that stores data relating to the individual's health. A manager device (e.g., within the platform 112) can create the LPR by compiling or aggregating received medical data (e.g., files) from numerous channels, including data already stored in the storage device, as will be described in greater detail below. The LPR can include patient demographics, encounters with care providers, patient vital signs gathered by care providers, medications prescribed to the patient, immunizations that the patient received, procedures performed on the patient, test results from tests performed on the patient, health goals set by the patient or the patient's care provider, care plans or medical treatment plans created by care providers for the patients, diagnoses or other health conditions of the patient, and social determinants of health. The LPR can further include data contributed by a user. For example, data contributed by a user can include information provided from a wearable or other device capable of providing health information. In some embodiments, the user may manually provide health information from an app or a website. The manager device can create the LPR in response to various external trigger messages, as will be described in more detail below. Additionally, the LPR can include a completeness score generated by the manager device or another device connected to the network. The completeness score can provide a numerical value indicative of the medical data's comprehensiveness and accuracy, which can provide added confidence to care providers seeking to use the LPR to learn about the patient before a patient arrives for medical care or to guide how medical care is to be administered. For example, an unconscious patient cannot answer medical history questions, so the doctor may rely on an LPR having a high completeness score to make informed medical decisions about the unconscious patient, which may save a patient's life (e.g., the doctor avoids certain medications identified as causing an allergy to the unconscious patient during the course of care). A completeness score for an individual can be based on the particular care path assigned to the patient's LPR. In an example embodiment, the completeness score can be weighted to reflect a particular procedure assigned to patient. In some circumstances a first completeness score relates to the overall health records of the patient and a second, specific procedure completeness score is assigned for a particular procedure/medical visit to be undertaken by the patient.

In one particular example, the manager device can create the LPR by aggregating or compiling patient data, claims data, and external data received from the health network utility in response to receiving an accept/discharge/transfer (ADT) message from a care provider on the network. In some embodiments, the ADT message comprises Health Level Seven (HL7) data transmitted on the network, and the ADT message can represent data associated with numerous medical events including admission of a patient to a care facility, discharging a patient from a care facility, changing an inpatient designation to an outpatient designation or vice versa, changing a patient ID, transferring a patient, or any other ADT message defined by HL7 or other protocol. The present system can be triggered to update the LPR upon an update to the patient record within a provider device or between provider devices. When different devices exchange patient related data, e.g., interface with each other, to send or receive new/updated patient data, that data is sent to the LPR.

The virtual charts comprise materialized views of data included in one or more than one LPRs. Said differently, each virtual chart can present data included in one or more than one LPRs and present the data in a specialized way according to preferences of a person or device that requested the virtual chart. For example, a first doctor may be an allergist, and the allergist may not need all medical data stored in the LPR, such as data submitted by an orthopedist, and so the virtual chart presented to the allergist may only contain some of the LPR data that is relevant to treating a patient's allergies. In another example, the manager device may generate a first virtual chart with medical data presented in a table form for a first data consumer (e.g., a first doctor), and the manager device may generate a second virtual chart with the same medical data presented as a graph for a second data consumer (e.g., a second doctor). The manager device may receive preferences from a data consumer, such as one of the provider devices or the user device, and generate a virtual chart in response to receiving those parameters or in response to other query information provided at the time the virtual chart was requested. In another embodiment, the preferences may be previously set and stored in the storage device. The virtual charts can also change in format depending on the time requested because medical data may have changed between a first virtual chart request and a second virtual chart request.

Example methods and systems for updating and curating data are described. More specifically, example methods and systems for receiving medical data from numerous sources or channels at defined trigger messages or events and curating the data at the defined trigger messages or events to create an LPR are described. Furthermore, example methods and systems for presenting updated and curated data according to user preferences is described. In the following description, for purposes of explanation, numerous specific details are set forth in order to provide a thorough understanding of example embodiments. It will be evident, however, to one of ordinary skill in the art that embodiments of the present disclosure may be practiced without these specific details.

Typically, medical data for an individual is scattered across numerous data storage locations controlled by various entities. For example, a hospital may store an EMR for an individual on a data storage device controlled by the hospital, and the hospital's EMR may store medical data related to an emergency room visit by the individual or surgery performed at the hospital on the individual. Meanwhile, a pharmacy may store prescription drug fulfillment history for the individual on a data storage device controlled by the pharmacy, and a primary care doctor may store vital sign information from yearly physicals administered to the individual on a data storage device controlled by the primary care physician's office. However, in this example, none of the hospital, the pharmacy, or the primary care physician has a complete medical record for the individual. In addition, medical data for the individual may be stale at one or more than one of the above-described entities. For example, the hospital may have vital sign data when a patient had a knee surgery operation in 2015, but the patient may have since developed a high blood pressure condition, rendering the hospital's blood pressure reading stale, outdated, and of little value.

Creating a single electronic health record for an individual reflecting all the medical events associated with the individual can be very difficult. To begin, a single entity would need to receive data from all care providers that provided care to the individual, and the single entity would need to convince every care provider to share this private medical data. Additionally, while medical data networks exist whereby entities, such as insurance companies or other care providers, can request information related to an individual, the information may not have a consistent format, may have incorrect, outdated, or conflicting information, or may simply be too much information for a single computer to manage. Said differently, gathering all EMRs associated with a single individual may not actually provide an accurate or complete health picture of the individual even using the existing networks and medical data sharing providers that currently exist. Thus, there is a need to curate all medical data associated with each individual in order to create a comprehensive and accurate EMR for individuals.

While some methods for curating data might exists, such curation methods are either use case based or constant. Constant medical data curation causes an incredible strain on data computing resources. Such constant medical data curation is costly because it requires frequent requests to either the provider devices or the health network utility, and requests to either of those entities may cost money to or impact the resources of the requester. In addition, even if a device associated with the requesting entity were able to make frequent, inexpensive or free requests for medical data, the processing power required to curate massive amounts of data would be unreasonably burdensome, particularly for a significantly large population of individuals, a population size that may be desirable to generate a large enough sample size to run certain analytic processes. For example, an insurance company may have millions of patients, and constantly curating medical data for millions of patients may not be feasible, efficient, or possible for even modern computing. Use case curation, on the other hand, may not generate an accurate snapshot of an individual's health because the curation is not run at appropriate times or might become stale very quickly. In either situation, better data curation methods are needed in the medical field (or any other field, such as government benefits, financial records, credit reports, etc.)

Finally, even if an entity were able to efficiently curate medical data from numerous sources or channels, the data must still be accurate enough to be useful for data consumers, such as care providers or insurance companies seeking to manage patient risk. That is, simply because an entity can combine medical data from multiple sources does not mean that the data is accurate or useful to other data consumers (e.g., doctors, care providers, pharmacies, etc.). Thus, the data must be curated in an effective manner so that the data reflects the most updated, most accurate, and most complete representation of an individual's health. If medical data created from multiple sources were not curated in this manner, the data consumers may not trust the data or may not find it useful for providing care, and the data consumers may try to acquire the medical data through other means (e.g., asking the patient to fill out numerous forms, generating the data themselves, etc.).

At the same time, any medical record must be complete to provide an accurate representation of the medical conditions and care, which requires management of both historical data and current state data. For example, an individual may have developed high blood pressure 10 years ago, but due to diet, exercise, lowered stress, medication, or all the above, the individual no longer suffers from high blood pressure. A complete medical record should store historical data because the individual was, at one time, diagnosed with high blood pressure, and knowing that medical history may be useful for some medical procedures or care. However, the medical record must also recognize the current state of the individual, whereby the individual's vital signs no longer exhibit high blood pressure. Thus, to generate a complete and accurate medical record, a computer would differentiate, categorize, and present data meaningfully, depending on context or preferences, so that a care provider or other data consumer can understand both the patient's medical history and current status. Moreover, data as presented should make sense to the recipient. For example, a patient may not understand medical data in the form of test readings and complicated medical terminology, whereas a doctor would. More granularly, a first doctor may not find all medical data associated with an individual relevant to his, her, or their practice, and so, irrelevant information should not be presented to every care provider. So, data presentation should account for the audience in how it is presented so that the data provided best communicates medical condition to a recipient.

The systems and methods described herein address the above-described issues by curating data in response to meaningful trigger messages. The trigger messages may be related to medical health events, which generate messages on medical networks, such as HL7 messages or any other protocol. For example, the trigger messages can include ADT messages, insurance claim submissions, appointment scheduling, and insurance eligibility submissions. By curating data in response to trigger messages, the processing load on the manager device is reduced so that data curation is only performed at meaningful times. Moreover, the identified trigger messages listed above represent that an individual is about to undergo medical care, is currently undergoing medical care, or recently received medical care, meaning that the trigger represents a significant and meaningful time in the health history of the patient. Thus, curating the data at that point indicates that any request made in response to the trigger should result in a complete medical picture for the individual. In response to one of the trigger messages, the systems and methods described herein can receive data from numerous sources, compiling or aggregating the received data, and curate the data, thereby creating an LPR.

The present machine learning systems and methods described herein can run on the LPR, which may provide insights for generating models of healthcare across populations and for specific individuals to be assigned care paths.

Glossary

"MACHINE-READABLE MEDIUM" in this context refers to a component, device, or other tangible media able to store instructions and data temporarily or permanently and may include, but is not limited to, random-access memory (RAM), read-only memory (ROM), buffer memory, flash memory, optical media, magnetic media, cache memory, other types of storage (e.g., Erasable Programmable Read-Only Memory (EEPROM)) and/or any suitable combination thereof. The term "machine-readable medium" should be taken to include a single medium or multiple media (e.g., a centralized or distributed database, or associated caches and servers) able to store instructions. The term "machine-readable medium" shall also be taken to include any medium, or combination of multiple media, that is capable of storing instructions (e.g., code) for execution by a machine, such that the instructions, when executed by one or more processors of the machine, cause the machine to perform any one or more of the methodologies described herein. Accordingly, a "machine-readable medium" refers to a single storage apparatus or device, as well as "cloud-based" storage systems or storage networks that include multiple storage apparatus or devices. The term "machine-readable medium" excludes signals per se.

"COMPONENT" in this context refers to a device, physical entity, or logic having boundaries defined by function or subroutine calls, branch points, APIs, or other technologies that provide for the partitioning or modularization of particular processing or control functions. Components may be combined via their interfaces with other components to carry out a machine process. A component may be a packaged functional hardware unit designed for use with other components and a part of a program that usually performs a particular function of related functions. Components may constitute either software components (e.g., code embodied on a machine-readable medium) or hardware components. A "hardware component" is a tangible unit capable of performing certain operations and may be configured or arranged in a certain physical manner. In various example embodiments, one or more computer systems (e.g., a stand-alone computer system, a client computer system, or a server computer system) or one or more hardware components of a computer system (e.g., a processor or a group of processors) may be configured by software (e.g., an application or application portion) as a hardware component that operates to perform certain operations as described herein.

A hardware component may also be implemented mechanically, electronically, or any suitable combination thereof. For example, a hardware component may include dedicated circuitry or logic that is permanently configured to perform certain operations. A hardware component may be a special-purpose processor, such as a Field-Programmable Gate Array (FPGA) or an ASIC. A hardware component may also include programmable logic or circuitry that is temporarily configured by software to perform certain operations. For example, a hardware component may include software executed by a general-purpose processor or other programmable processor. Once configured by such software, hardware components become specific machines (or specific components of a machine) uniquely tailored to perform the configured functions and are no longer general-purpose processors. It will be appreciated that the decision to implement a hardware component mechanically, in dedicated and permanently configured circuitry, or in temporarily configured circuitry (e.g., configured by software) may be driven by cost and time considerations. Accordingly, the phrase "hardware component" (or "hardware-implemented component") should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware components are temporarily configured (e.g., programmed), each of the hardware components need not be configured or instantiated at any one instance in time. For example, where a hardware component comprises a general-purpose processor configured by software to become a special-purpose processor, the general-purpose processor may be configured as respectively different special-purpose processors (e.g., comprising different hardware components) at different times. Software accordingly configures a particular processor or processors, for example, to constitute a particular hardware component at one instance of time and to constitute a different hardware component at a different instance of time.

Hardware components can provide information to, and receive information from, other hardware components. Accordingly, the described hardware components may be regarded as being communicatively coupled. Where multiple hardware components exist contemporaneously, communications may be achieved through signal transmission (e.g., over appropriate circuits and buses) between or among two or more of the hardware components. In embodiments in which multiple hardware components are configured or instantiated at different times, communications between such hardware components may be achieved, for example, through the storage and retrieval of information in memory structures to which the multiple hardware components have access. For example, one hardware component may perform an operation and store the output of that operation in a memory device to which it is communicatively coupled. A further hardware component may then, at a later time, access the memory device to retrieve and process the stored output.

Hardware components may also initiate communications with input or output devices and can operate on a resource (e.g., a collection of information). The various operations of example methods described herein may be performed, at least partially, by one or more processors that are temporarily configured (e.g., by software) or permanently configured to perform the relevant operations. Whether temporarily or permanently configured, such processors may constitute processor-implemented components that operate to perform one or more operations or functions described herein. As used herein, "processor-implemented component" refers to a hardware component implemented using one or more processors. Similarly, the methods described herein may be at least partially processor-implemented, with a particular processor or processors being an example of hardware. For example, at least some of the operations of a method may be performed by one or more processors or processor-implemented components. Moreover, the one or more processors may also operate to support performance of the relevant operations in a "cloud computing" environment or as a "software as a service" (SaaS). For example, at least some of the operations may be performed by a group of computers (as examples of machines including processors), with these operations being accessible via a network (e.g., the Internet) and via one or more appropriate interfaces (e.g., an API). The performance of certain of the operations may be distributed among the processors, not only residing within a single machine, but deployed across a number of machines. In some example embodiments, the processors or processor-implemented components may be located in a single geographic location (e.g., within a home environment, an office environment, or a server farm). In other example embodiments, the processors or processor-implemented components may be distributed across a number of geographic locations.

"PROCESSOR" in this context refers to any circuit or virtual circuit (a physical circuit emulated by logic executing on an actual processor) that manipulates data values according to control signals (e.g., "commands," "op codes," "machine code," etc.) and which produces corresponding output signals that are applied to operate a machine. A processor may, for example, be a CPU, a RISC processor, a CISC processor, a GPU, a DSP, an ASIC, a RFIC, or any combination thereof. A processor may further be a multi-core processor having two or more independent processors (sometimes referred to as "cores") that may execute instructions contemporaneously.

The term "coupled" can be used herein to refer to any type of relationship, direct or indirect, between the components in question, and can apply to electrical, mechanical, fluid, optical, electromagnetic, electromechanical or other connections. In addition, the terms "first", "second", etc. can be used herein only to facilitate discussion, and carry no particular temporal or chronological significance unless otherwise indicated.

Changes and modifications may be made to the disclosed embodiments without departing from the scope of the present disclosure. These and other changes or modifications are intended to be included within the scope of the present disclosure, as expressed in the following claims. Those skilled in the art will appreciate from the foregoing description that the broad techniques of the embodiments of the present disclosure can be implemented in a variety of forms. Therefore, while the embodiments of this disclosure have been described in connection with particular examples thereof, the true scope of the embodiments of the disclosure should not be so limited since other modifications will become apparent to the skilled practitioner upon a study of the drawings, specification, and following claims.

The Abstract of the Disclosure is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

We claim:

1. A computing system comprising:
a processor; and
a memory having a set of instructions, which when executed by the processor, cause the computing system to:
train a machine learning question and recommendation model (MLQRM) to map recommendations into a vector space as recommendation vectors, wherein to train the MLQRM, the set of instructions when executed, cause the computing system to train the MLQRM based on user responses to questions by patients, recommendations to the patients, and engagement data identifying engagements of the patients with the recommendations, wherein the recommendations mitigate health conditions;
receive a user request from a user device;
identify that a plurality of questions is available for presentation on the user device based on the user request;
select a first question from the plurality of questions;
transmit the first question to the user device;
receive a first user reply from the user device, wherein the first user reply is an answer to the first question;

generate, with a generative artificial intelligence model of the MLQRM, a second question based on the first user reply and the first question;
transmit the second question to the user device;
receive a second user reply from the user device, wherein the second user reply is an answer to the second question;
generate, with the MLQRM, a user vector based on the first and second user replies;
determine, with the MLQRM, a user suggestion from the plurality of recommendations based on a similarity between the recommendation vectors and the user vector; and
transmit the user suggestion to the user device.

2. The computing system of claim 1, wherein the instructions of the memory, when executed, cause the computing system to:
transmit the first question, the second question, and the user suggestion to the user device via an application programming interface.

3. The computing system of claim 1, wherein the instructions of the memory, when executed, cause the computing system to:
receive the first user reply and the second user reply via an application programming interface.

4. The computing system of claim 1, wherein the instructions of the memory, when executed, cause the computing system to:
execute an authentication process on a current user associated with the user device to authenticate the current user; and
determine that communication with the current user is to be executed in response to the current user being authenticated.

5. The computing system of claim 1, wherein the instructions of the memory, when executed, cause the computing system to:
encrypt the first question, the second question, and the user suggestion prior to transmission to the user device.

6. The computing system of claim 1, wherein the instructions of the memory, when executed, cause the computing system to:
decrypt data from the user device to extract the first user reply and the second user reply.

7. The computing system of claim 1, wherein the instructions of the memory, when executed, cause the computing system to:
gather the user responses, and the engagement data; and;
translate, with the MLQRM, the user responses into the vector space to generate recommendation vectors.

8. The computing system of claim 7, wherein to determine the user suggestion, the MLQRM is configured to:
calculate one or more differences between the recommendation vectors and the user vectors; and
select the user suggestion based on the one or more differences.

9. The computing system of claim 8, wherein to determine the user suggestion, the MLQRM is configured to:
identify a lowest difference from the one or more differences, wherein the user suggestion is associated with the lowest difference.

10. The computing system of claim 1, wherein the instructions of the memory, when executed, cause the computing system to:
retrieve user data, wherein the user data includes implicit feedback associated with a current user and explicit feedback associated with the current user, wherein the current user is associated with the user device, and further wherein the MLQRM determines the user suggestion further based on the implicit feedback and the explicit feedback.

11. The computing system of claim 1, wherein the generative artificial intelligence model generates the second question, with a variational autoencoder.

12. The computing system of claim 1, wherein the instructions of the memory, when executed, cause the computing system to:

determine that the second user reply is to be converted into an observation, wherein the observation is a qualitative representation of the second user reply;

initiate an asynchronous state machine based on the second user reply being determined to be converted into the observation;

convert the second user reply into the observation with the asynchronous state machine; and cause a third question from the plurality of questions to be presented on the user device as the asynchronous state machine is executed.

13. The computing system of claim 1, wherein the user suggestion includes one or more of a first suggested service, a first application, or a first website.

14. The computing system of claim 13, wherein the instructions of the memory, when executed, cause the computing system to:

determine that one or more of a second service, a second application, or a second website is to be bypassed for the user suggestion.

15. The computing system of claim 1, wherein the instructions of the memory, when executed, cause the computing system to:

access one or more of rules, a linear ordering, or a state machine to select the first question.

16. The computing system of claim 1, wherein the instructions of the memory, when executed, cause the computing system to:

identify user information associated with a current user, wherein the current user is associated with the user device, wherein the user information includes one or more of identifying information of the current user or user measurements of the current user; and determine whether to select a third question of the plurality of questions for transmission to the user device based on whether a third answer to the third question is contained within the user information.

17. The computing system of claim 1, wherein the first question, the second question, the first user reply, and the second user reply comply with a Fast Healthcare Interoperability Resources standard.

18. The computing system of claim 1, wherein to determine the user suggestion, the set of instructions, which when executed by the processor, cause the computing system to identify the user suggestion with the generative machine learning model.

19. At least one non-transitory computer readable storage medium comprising a set of instructions, which when executed by a computing system, cause the computing system to:

train a machine learning question and recommendation model (MLQRM) to map recommendations into a vector space as recommendation vectors, wherein to train the MLQRM, the set of instructions when executed, cause the computing system to train the MLQRM based on user responses to questions by patients, recommendations to the patients, and engagement data identifying engagements of the patients with the recommendations, wherein the recommendations mitigate health conditions;

receive a user request from a user device;

identify that a plurality of questions is available for presentation on the user device based on the user request;

select a first question from the plurality of questions;

transmit the first question to the user device;

receive a first user reply from the user device, wherein the first user reply is an answer to the first question;

generate, with a generative artificial intelligence model of the MLQRM, a second question based on the first user reply and the first question;

transmit the second question to the user device;

receive a second user reply from the user device, wherein the second user reply is an answer to the second question;

generate, with the MLQRM, a user vector based on the first and second user replies;

determine, with the MLQRM, a user suggestion from the plurality of recommendations based on a similarity between the recommendation vectors and the user vector; and transmit the user suggestion to the user device.

20. A method comprising:

training a machine learning question and recommendation model (MLQRM) to map recommendations into a vector space as recommendation vectors, wherein the training includes training the MLQRM based on user responses to questions by patients, recommendations to the patients, and engagement data identifying engagements of the patients with the recommendations, wherein the recommendations mitigate health conditions;

receiving a user request from a user device;

identifying that a plurality of questions is available for presentation on the user device based on the user request;

selecting a first question from the plurality of questions;

transmitting the first question to the user device;

receiving a first user reply from the user device, wherein the first user reply is an answer to the first question;

generating, with a generative artificial intelligence model of the MLQRM, a second question based on the first user reply and the first question;

transmitting the second question to the user device;

receiving a second user reply from the user device, wherein the second user reply is an answer to the second question;

generating, with the MLQRM, a user recommendation based on the first and second user replies;

determining, with the MLQRM, a user recommendation from the plurality of recommendations based on a similarity between the recommendation vectors and the user vector; and transmitting the user suggestion to the user device.

* * * * *